United States Patent
Huang et al.

(10) Patent No.: US 10,633,337 B2
(45) Date of Patent: Apr. 28, 2020

(54) CRYSTAL FORMS OF A 9-AMINOMETHYL SUBSTITUTED TETRACYCLINE COMPOUND AND A PREPARATION METHOD THEREOF

(71) Applicant: KBP Biosciences Co., Ltd., Jinan, Shandong (CN)

(72) Inventors: Zhenhua Huang, Shandong (CN); Mei Hong, Shandong (CN); Chen Jiang, Shandong (CN)

(73) Assignee: KBP Biosciences Co., Ltd., Jinan, Shandong (CN)

( * ) Notice: Subject to any disclaimer, the term of this patent is extended or adjusted under 35 U.S.C. 154(b) by 0 days.

(21) Appl. No.: 16/312,404

(22) PCT Filed: Jun. 22, 2017

(86) PCT No.: PCT/CN2017/089470
§ 371 (c)(1),
(2) Date: Dec. 21, 2018

(87) PCT Pub. No.: WO2017/219994
PCT Pub. Date: Dec. 28, 2017

(65) Prior Publication Data
US 2019/0241515 A1    Aug. 8, 2019

(30) Foreign Application Priority Data

Jun. 22, 2016    (CN) .......................... 2016 1 0457261

(51) Int. Cl.
| | | |
|---|---|---|
| C07D 209/02 | (2006.01) | |
| A61P 31/04 | (2006.01) | |
| A61K 31/65 | (2006.01) | |
| A61P 35/00 | (2006.01) | |
| A61P 3/10 | (2006.01) | |
| C07D 209/54 | (2006.01) | |
| A61P 31/00 | (2006.01) | |

(52) U.S. Cl.
CPC ............ *C07D 209/02* (2013.01); *A61K 31/65* (2013.01); *A61P 3/10* (2018.01); *A61P 31/00* (2018.01); *A61P 31/04* (2018.01); *A61P 35/00* (2018.01); *C07D 209/54* (2013.01); *C07B 2200/13* (2013.01)

(58) Field of Classification Search
None
See application file for complete search history.

(56) References Cited

U.S. PATENT DOCUMENTS 9,365,499 B2 *  6/2016  Zhang .................. C07D 221/20
2014/0179638 A1   6/2014  Zhang et al.

FOREIGN PATENT DOCUMENTS

| CN | 102417465 A | 4/2012 |
| CN | 103717571 B | 1/2016 |
| WO | 2013/013505 A1 | 1/2013 |

OTHER PUBLICATIONS

International Search Report of the State Intellectual Property Office of the Peoples Republic of China dated Sep. 22, 2017 for International Application No. PCT/CN2017/089470, 2 pages.

* cited by examiner

*Primary Examiner* — Kamal A Saeed
(74) *Attorney, Agent, or Firm* — Fitch, Even, Tabin & Flannery, LLP

(57) ABSTRACT

The present invention belongs to the field of pharmaceutical technology, and crystal forms of a 9-aminomethyl substituted tetracycline compound and a process for preparing the same. More specifically, the present invention relates to crystal forms of the compound represented by formula (1), a process for preparing crystal forms of the compound represented by formula (1) and use of said crystal forms in manufacture of medicament for treating and/or preventing an infection disease caused by tetracycline-sensitive bacteria and/or tetracycline-resistant bacteria.

Formula (1)

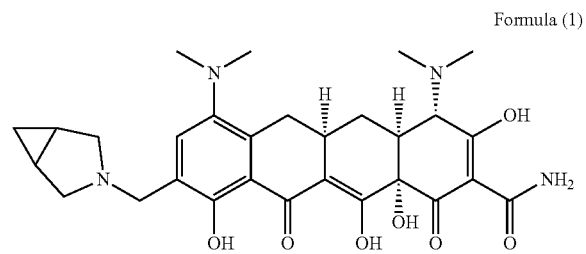

10 Claims, 14 Drawing Sheets

CRYSTAL FORMS OF A 9-AMINOMETHYL SUBSTITUTED TETRACYCLINE COMPOUND AND A PREPARATION METHOD THEREOF

CROSS-REFERENCE TO RELATED APPLICATIONS

This application is a U.S. national phase application filed under 35 U.S.C. § 371 of International Application Number PCT/CN2017/089470, filed Jun. 22, 2017, designating the United States, which claims priority from Chinese Patent Application Number 201610457261.5, filed Jun. 22, 2016.

TECHNICAL FIELD

The present invention relates to crystal forms of a 9-aminomethyl substituted tetracycline compound and a preparation method thereof, and use of crystal forms of the compound in manufacture of a medicament for treating and/or preventing a disease caused by tetracycline-sensitive bacteria and/or tetracycline-resistant bacteria.

BACKGROUND ART

Tetracycline antibiotics are a kind of broad-spectrum antibiotics for oral use, which are generated by *Actinomycete-Streptomyces* fermentation. They have good pharmacological action against *rickettsia*, many Gram-positive and Gram-negative bacteria, lymphogranuloma venereum pathogens, inclusion conjunctivitis pathogens and psittacosis pathogens.

In the early 1990s, a class of new tetracycline drugs (named as glycyclines) was developed, and its representative drug was tigecycline (GAR-936), which had broad antibacterial spectrum. Tigecycline not only has the same antibacterial activity as the previous tetracyclines, but also has an antibacterial activity to the pathogens that have been resistant to tetracyclines due to efflux mechanism and ribosomal protection mechanisms. Up to now, no oral tigecycline drug can be available in the market.

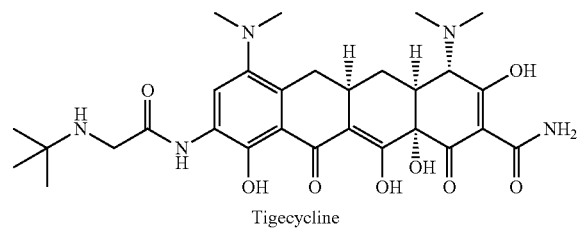 [SMILES: CN(C)c1cc(NC(=O)CNC(C)(C)C)c(O)c2c1C[C@H]1C[C@H]3[C@H](N(C)C)C(O)=C(C(N)=O)C(=O)[C@@]3(O)C(O)=C1C2=O]

Tigecycline

In addition, WO2013013505 A1 discloses a compound represented by the following formula (I),

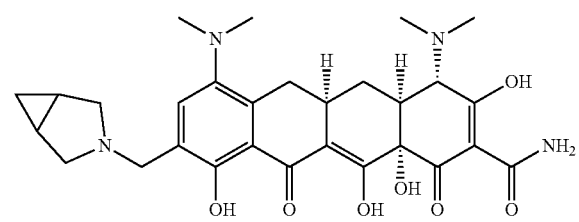

Formula (1)

Its chemical name is (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide. This compound has a broad antibacterial spectrum and a high antibacterial activity.

WO2013013505 A1 further discloses a preparation process for the compound represented by formula (1). Said process can produce an amorphous form of the compound represented by formula (1) (FIG. 13), but cannot produce any crystal form of the compound represented by formula (1).

SUMMARY OF THE INVENTION

In the process of studying and developing the compound represented by formula (1), it is found that the compound represented by formula (1) is prone to form an unstable solvate, resulting in an unsatisfactory purity, content and stability. In order to obtain crystal forms with high purity, high content and good stability, the present inventors have made a deep study on crystal forms of the compound represented by formula (1), and finally found crystal forms of the compound represented by formula (1).

An object of the present invention is to provide crystal forms of the compound represented by formula (1).

Another object of the present invention is to provide pharmaceutically acceptable crystal forms of the compound represented by formula (1).

Another object of the present invention is to provide a method for preparing crystal forms of the compound represented by formula (1) and a method for converting any one of crystal forms into another crystal form.

Another object of the present invention is to provide use of crystal forms of the compound represented by formula (1) in a medicament for preventing and/or treating a disease caused by tetracycline-sensitive bacteria and/or tetracycline-resistant bacteria, wherein said disease caused by tetracycline-sensitive bacteria and/or tetracycline-resistant bacteria is for example infection, cancer, diabetes and other diseases that have been found to be treatable and/or preventable by other tetracycline compounds.

The present inventors have made a deep study on crystal forms of the compound represented by formula (1) and found:

(1) Amorphous Form

The preparation process as described in WO2013013505 A1 produces amorphous form of the compound represented by formula (1), which has an XRPD spectrum as shown in FIG. 13.

Amorphous form of the compound represented by formula (1) has a lower content and is not easy to be purified. In the process as described in Example 1, a first purification by column chromatography of the crude product results in a content of 84.8%, a second purification results in a content of 87.7%, and the content after several purifications still cannot satisfy the requirement of the pharmaceutical manufacture.

It is also found in the study that amorphous form of the compound represented by formula (1) has a poor stability, as shown in table 1, the content after 14 days at a high temperature of 60° C. reduces by 6.6%, the content after 14 days at a high humidity condition of 40° C./75%±5% RH reduces by 7.5%, and the content after 14 days under an illumination condition of 4500 lx±500 lx reduces by 12.1%. Amorphous form of the compound represented by formula (1) itself has a lower content in its preparation, and has poor stabilities at a high temperature, at high humidity and under an illumination condition. Therefore, amorphous form of the compound represented by formula (1) is not suitable for the pharmaceutical manufacture.

In summary, amorphous form of the compound represented by formula (1) cannot satisfy the requirement of the pharmaceutical manufacture, and there is an urgent need to find a pharmaceutical acceptable crystal form having a better purity, content and stability.

(2) Crystal Forms

The present inventors have further made a vast of research on crystal forms of the compound represented by formula (1), and found crystal forms I, II, III, IV, V, VI, VII, VIII of the compound represented by formula (1). It is necessary to particularly point out, these eight different crystal forms cannot be predicted according to the chemical formula of the compound represented by formula (1), and the structure or property of any of these crystal forms cannot be predicated either.

Crystal forms of the compound represented by formula (1) have X-ray powder diffraction patterns comprising the following characteristic peaks expressed by 2θ degree, when measured using Cu-Ka radiation:

Crystal form I: 10.6°±0.2°, 13.3°±0.2°, 15.9°±0.2°, 24.0°±0.2°;
Crystal form II: 10.2°±0.2°, 15.9°±0.2°, 17.9°±0.2°, 24.1°±0.2°;
Crystal form III: 11.7°±0.2°, 16.6°±0.2°, 20.5°±0.2°, 27.3°±0.2°;
Crystal form IV: 6.8°±0.2°, 10.0°±0.2°, 11.1°±0.2°, 21.5°±0.2°;
Crystal form V: 9.7°±0.2°, 17.9°±0.2°, 19.2°±0.2°, 23.8°±0.2°;
Crystal form VI: 7.7°±0.2°, 15.5°±0.2°, 15.9°±0.2°, 19.5°±0.2°;
Crystal form VII: 11.7°±0.2°, 15.1°±0.2°, 15.9°±0.2°, 17.9°±0.2°;
Crystal form VIII: 4.8°±0.2°, 9.7°±0.2°, 19.6°±0.2°.

Said crystal forms of the compound represented by formula (1) have X-ray powder diffraction patterns comprising the following characteristic peaks expressed by 2θ degree, when measured using Cu-Ka radiation:

Crystal form I: 9.0°±0.2°, 10.6°±0.2°, 13.3°±0.2°, 15.9°±0.2°, 23.6°±0.2°, 24.0°±0.2°;
Crystal form II: 9.3°±0.2°, 10.2°±0.2°, 14.0°±0.2°, 15.9°±0.2°, 17.9°±0.2°, 24.1°±0.2°;
Crystal form III: 9.5°±0.2°, 11.7°±0.2°, 16.6°±0.2°, 20.5°±0.2°, 22.1°±0.2°, 27.3°±0.2°;
Crystal form IV: 6.8°±0.2°, 10.0°±0.2°, 11.1°±0.2°, 20.1°±0.2°, 20.5°±0.2°, 21.5°±0.2°;
Crystal form V: 9.7°±0.2°, 11.8°±0.2°, 17.9°±0.2°, 19.2°±0.2°, 22.1°±0.2°, 23.8°±0.2°;
Crystal form VI: 7.7°±0.2°, 15.5°±0.2°, 15.9°±0.2°, 17.2°±0.2°, 19.5°±0.2°, 21.2°±0.2°;
Crystal form VII: 11.7°±0.2°, 15.1°±0.2°, 15.9°±0.2°, 17.9°±0.2°, 20.1°±0.2°, 21.8°±0.2°;
Crystal form VIII: 4.8°±0.2°, 9.7°±0.2°, 14.6°±0.2°, 19.6°±0.2°, 22.0°±0.2°, 24.5°±0.2°.

Said crystal forms of the compound represented by formula (1) have X-ray powder diffraction patterns comprising the following characteristic peaks expressed by 2θ degree, when measured using Cu-Ka radiation:

Crystal form I: 9.0°±0.2°, 10.6°±0.2°, 13.3°±0.2°, 14.3°±0.2°, 15.9°±0.2°, 18.0°±0.2°, 20.0°±0.2°, 21.3°±0.2°, 23.6°±0.2°, 24.0°±0.2°;
Crystal form II: 9.3°±0.2°, 10.2°±0.2°, 14.0°±0.2°, 15.9°±0.2°, 17.9°±0.2°, 20.8°±0.2°, 23.0°±0.2°, 24.1°±0.2°, 24.8°±0.2°, 27.7°±0.2°;
Crystal form III: 9.5°±0.2°, 11.7°±0.2°, 12.7°±0.2°, 13.5°±0.2°, 16.6°±0.2°, 19.8°±0.2°, 20.5°±0.2°, 22.1°±0.2°, 23.5°±0.2°, 27.3°±0.2°, 27.7°±0.2°;
Crystal form IV: 6.8°±0.2°, 10.0°±0.2°, 11.1°±0.2°, 11.8°±0.2°, 13.9°±0.2°, 14.9°±0.2°, 15.5°±0.2°, 20.1°±0.2°, 20.5°±0.2°, 21.5°±0.2°;
Crystal form V: 7.1°±0.2°, 9.7°±0.2°, 11.8°±0.2°, 16.5°±0.2°, 17.9°±0.2°, 19.2°±0.2°, 22.1°±0.2°, 23.1°±0.2°, 23.8°±0.2°, 24.9°±0.2°;
Crystal form VI: 7.7°±0.2°, 15.5°±0.2°, 15.9°±0.2°, 17.2°±0.2°, 18.0°±0.2°, 19.5°±0.2°, 20.6°±0.2°, 21.2°±0.2°, 22.0°±0.2°, 29.5°±0.2°;
Crystal form VII: 11.0°±0.2°, 11.7°±0.2°, 13.8°±0.2°, 14.3°±0.2°, 15.1°±0.2°, 15.9°±0.2°, 17.9°±0.2°, 20.1°±0.2°, 21.8°±0.2°, 25.6°±0.2°;
Crystal form VIII: 4.8°±0.2°, 9.7°±0.2°, 14.6°±0.2°, 19.6°±0.2°, 22.0°±0.2°, 24.5°±0.2°.

Among crystal forms of the compound represented by formula (1),

Crystal form I has an endothermic peak in the range of 180-220° C. in its differential scanning calorimetry curve;
Crystal form II has an endothermic peak in the range of 195-215° C. in its differential scanning calorimetry curve;
Crystal form III has an endothermic peak in the range of 150-190° C. in its differential scanning calorimetry curve;
Crystal form VII has an endothermic peak in the range of 165-205° C. in its differential scanning calorimetry curve.

Crystal forms of the compound represented by formula (1), which are characterized respectively in that, Crystal form I has an X-ray powder diffraction pattern as shown in FIG. 1;
Crystal form II has an X-ray powder diffraction pattern as shown in FIG. 3;
Crystal form III has an X-ray powder diffraction pattern as shown in FIG. 5;
Crystal form IV has an X-ray powder diffraction pattern as shown in FIG. 7;
Crystal form V has an X-ray powder diffraction pattern as shown in FIG. 8;
Crystal form VI has an X-ray powder diffraction pattern as shown in FIG. 9;
Crystal form VII has an X-ray powder diffraction pattern as shown in FIG. 10;
Crystal form VIII has an X-ray powder diffraction pattern as shown in FIG. 12.

Preparation method for crystal form I of the compound represented by formula (1): the compound represented by formula (1) is placed in anhydrous acetonitrile for slurry-washing or in tetrahydrofuran for stirring, a solid separates from the mixture, and crystal form I is obtained through filtration.

Preparation method for crystal form II of the compound represented by formula (1): the compound represented by formula (1) is placed in a mixed solution of a lower alcohol or ethyl acetate or acetone or methanol and water (1:1-9:1, v/v) for slurry-washing, or dissolved in tetrahydrofuran under an atmosphere of isopropanol or n-heptane, a solid separates from the mixture, and crystal form II is obtained through filtration.

Preparation method for crystal form III of the compound represented by formula (1): the compound represented by formula (1) is placed in a mixed solution of acetonitrile and water in a ratio of 1:1-4:1 for slurry-washing at 0-70° C., and crystal form III is obtained through filtration, as acetonitrile solvate.

Preparation method for crystal form IV of the compound represented by formula (1): the compound represented by formula (1) is placed in a mixed solution of acetonitrile and water in a ratio of 9:1 for slurry-washing at 70-90° C. to produce crystal form IV.

Preparation method for crystal form II of the compound represented by formula (1): the compound represented by formula (1) is placed in a lower alcohol, ethyl acetate, acetone, or a mixed solution of methanol and water (1:1-9:1, v/v) for slurry-washing, or dissolved in tetrahydrofuran under an atmosphere of isopropanol or n-heptane, a solid separates from the mixture, and crystal form II is obtained through filtration.

Preparation method for crystal form VI of the compound represented by formula (1): the compound represented by formula (1) is placed in chloroform solution for slow volatilization; or the compound represented by formula (1) is dissolved in chloroform, placed in an atmosphere of isopropanol or n-heptane, and a solid separates from the mixture; or the compound represented by formula (1) is dissolved in chloroform, under the induction of polyvinyl acetate, polyphenylene sulfide, 1,3-dimethylimidazoline mesylate or 1,3-dimethylimidazoline perchlorate, chloroform is volatilized, a solid separates from the mixture to produce crystal form VI as chloroform solvate.

Preparation method for crystal form VII of the compound represented by formula (1): the compound represented by formula (1) is placed in a mixed solution of acetonitrile and water in a ratio of 1:1-9:1 (v/v) for slurry-washing, filtered, and dried in vacuum to produce crystal form VII. Alternatively, crystal form III of the compound represented by formula (1) is dried in vacuum to produce crystal form VII.

Preparation method for crystal form VIII of the compound represented by formula (1): the compound represented by formula (1) is placed in isopropyl acetate for slurry-washing, and filtered to produce crystal form VIII as isopropyl acetate solvate.

It is found in a further study that, the above crystal forms III, V, VI and VIII are solvates, and respectively contain non-pharmaceutically acceptable organic solvents, acetonitrile (Class 2 solvent, concentration limit: 410 ppm), chloroform (Class 2 solvent, concentration limit: 60 ppm), and isopropyl acetate (Class 3 solvent, the amount of residual solvent is not more than 0.5%). By measurement, crystal forms III, V, VI and VIII have the residual solvent concentration beyond the pharmaceutically acceptable limits and do not conform to the pharmaceutical requirement.

In order to further measure the stability of the amorphous form in conformity with the pharmaceutical acceptable content, it is necessary to prepare the amorphous form having a high content. According to the present invention, the amorphous form having a high pharmaceutical acceptable content (the content is 97.1%) is prepared from the crystal form of the compound represented by formula (1) having a high content as the starting material, and it is found that the content of the amorphous form is reduced in the conversion process (as shown in Example 1).

It is also found in the study that not all of crystal forms I, II, III, IV, V, VI, VII and VIII of the compound represented by formula (1) have better stability than the amorphous form. Specifically, in the investigation of the stability of crystal form III, the content of the compound is reduced by about 10% after being placed in a high humidity condition of 40° C./75%±5% RH for 14 days. It can be seen that in a high humidity condition, crystal form III has worse stability than the amorphous form. In addition, in the investigation of the stability of crystal form IV, the content is reduced by 23.1% after being placed in an illumination condition of 4500 Lx±500 Lx for 15 days, and additionally the content is reduced by nearly 10% after being placed at a high temperature of 60° C. for 15 days. The above test results show that crystal form IV has worse stability than the amorphous form in the illumination condition or the high temperature condition.

Therefore, not all of crystal forms I, II, III, IV, V, VI, VII and VIII of the compound represented by formula (1) can satisfy the pharmaceutical requirements.

(3) Pharmaceutically Acceptable Crystal Forms

Based on the above study, the present invention provides the stable crystal form I, the stable crystal form II and the stable crystal form VII of the compound represented by formula (1).

The preferable technical solutions of the present invention are as follows:

Crystal forms of the compound represented by formula (1) (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide, have X-ray powder diffraction patterns comprising the following characteristic peaks expressed by 2θ degree, when measured using Cu-Ka radiation:

Crystal form I: 10.6°±0.2°, 13.3°±0.2°, 15.9°±0.2°, 24.0°±0.2°;
Crystal form II: 10.2°±0.2°, 15.9°±0.2°, 17.9°±0.2°, 24.1°±0.2°;
Crystal form VII: 11.7°±0.2°, 15.1°±0.2°, 15.9°±0.2°, 17.9°±0.2°.

Crystal forms of the compound represented by formula (1) have X-ray powder diffraction patterns comprising the following characteristic peaks expressed by 2θ degree, when measured using Cu-Ka radiation:

Crystal form I: 9.0°±0.2°, 10.6°±0.2°, 13.3°±0.2°, 15.9°±0.2°, 23.6°±0.2°, 24.0°±0.2°;
Crystal form II: 9.3°±0.2°, 10.2°±0.2°, 14.0°±0.2°, 15.9°±0.2°, 17.9°±0.2°, 24.1°±0.2°;
Crystal form VII: 11.7°±0.2°, 15.1°±0.2°, 15.9°±0.2°, 17.9°±0.2°, 20.1°±0.2°, 21.8°±0.2°.

Crystal forms of the compound represented by formula (1) have X-ray powder diffraction patterns comprising the following characteristic peaks expressed by 2θ degree, when measured using Cu-Ka radiation:

Crystal form I: 9.0°±0.2°, 10.6°±0.2°, 13.3°±0.2°, 14.3°±0.2°, 15.9°±0.2°, 18.0°±0.2°, 20.0°±0.2°, 21.3°±0.2°, 23.6°±0.2°, 24.0°±0.2°;
Crystal form II: 9.3°±0.2°, 10.2°±0.2°, 14.0°±0.2°, 15.9°±0.2°, 17.9°±0.2°, 20.8°±0.2°, 23.0°±0.2°, 24.1°±0.2°, 24.8°±0.2°, 27.7°±0.2°;
Crystal form VII: 11.0°±0.2°, 11.7°±0.2°, 13.8°±0.2°, 14.3°±0.2°, 15.1°±0.2°, 15.9°±0.2°, 17.9°±0.2°, 20.1°±0.2°, 21.8°±0.2°, 25.6°±0.2°.

Among crystal forms of the compound represented by formula (1),

Crystal form I has an endothermic peak in the range of 180-220° C. in its differential scanning calorimetry curve;
Crystal form II has an endothermic peak in the range of 195-215° C. in its differential scanning calorimetry curve;
Crystal form VII has an endothermic peak in the range of 165-205° C. in its differential scanning calorimetry curve.

Crystal forms of the compound represented by formula (1), which are characterized respectively in that, Crystal form I has an X-ray powder diffraction pattern as shown in FIG. 1;
Crystal form II has an X-ray powder diffraction pattern as shown in FIG. 3;
Crystal form VII has an X-ray powder diffraction pattern as shown in FIG. 10.

The present invention further provides a pharmaceutical composition, said pharmaceutical composition contains amorphous or crystal forms of the compound represented by formula (1), and pharmaceutically acceptable carriers, wherein said crystal forms comprise crystal form I, II, VII or a combination thereof.

In the pharmaceutical composition of the present invention, said crystal form is present in a pure form. Including but not exclusively, the content of crystal form I, II, VII or a combination thereof is not lower than 94.5% or 95% or 96% or 98% or 99%, for example, less than about 5.5%, less than about 5%, less than about 4%, less than about 2% or less than about 1% of the impurities are present. The impurities include but are not limited to degradation products, oxidation products, epimers, solvents and/or other undesirable impurities.

The present invention further provides a pharmaceutical acceptable formulation of crystal forms of the compound represented by formula (1) and one or more pharmaceutically acceptable carriers and/or diluents, which can be any pharmaceutical acceptable dosage form. The present invention further provides a pharmaceutical acceptable formulation that can be prepared from crystal forms of the compound represented by formula (1) and one or more pharmaceutically acceptable carriers. Said pharmaceutical formulation refers to conventional formulations in the clinical use, and can be orally or parenterally applied to patients in need of such treatment. For oral administration, they can be made into conventional solid formulations such as tablets, capsules, pills, granules, etc., as well as oral liquid formulations, such as oral solutions, oral suspensions, syrups, etc. For parenteral administration, they can be made into injections, including injection solution, a sterile powder for injection, concentrated solution for injection and suspension for injection. For rectal administration, they can be made into suppositories and the like. For transpulmonary administration, they can be made into inhalations or aerosols and the like. For topical or percutaneous administration, they can be made into ointments, pastes, creams, lotions, gels, powders, solutions or transdermal stickers and the like. These formulations can be prepared by conventional methods, which comprise a step of adding pharmaceutically acceptable carriers such as excipients, binders, moisturizers, disintegrating agents, thickeners and the like. Said crystal forms comprise crystal form I, II, VII or a combination thereof.

The present invention further provides use of crystal forms of the compound represented by formula (1) in manufacture of a medicament for treating and/or preventing a disease caused by tetracycline-sensitive bacteria and/or tetracycline-resistant bacteria, wherein said "disease caused by tetracycline-sensitive bacteria and/or tetracycline-resistant bacteria" is for example infection, cancer, diabetes and other diseases that have been found to be treatable and/or preventable by other tetracycline compounds, wherein said crystal forms include crystal form I, II, VII or a combination thereof.

Crystal forms of the compound represented by formula (1) of the present invention can be used to treat and/or prevent tetracycline drug-sensitive diseases including infections (e.g. rickettsial infection, lymphogranuloma venereum, inclusion conjunctivitis, psittacosis pathogens infection and other tetracycline compound resistant infections), cancers, diabetes and any other diseases that have been found to be treatable and/or preventable by tetracycline compounds. Crystal forms of the compound represented by formula (1) of the present invention have a broad antibacterial spectrum and strong antibacterial activity against both Gram-positive and -negative bacteria, including aerobic and anaerobic bacteria, and further have good pharmacokinetics.

Compared with the closest prior art, crystal forms of the compound represented by formula (1) of the present invention has the following advantages:

(1) crystal form I, II, VII of the compound represented by formula (1) according to the present invention or a combination thereof has good stability, wherein crystal forms I and II have better stability than crystal form VII, and crystal form I has better thermal stability than crystal form II;

(2) crystal form I, II, VII of the compound represented by formula (1) according to the present invention or a combination thereof has a lower amount of residual solvent, and therefore low toxicity and side-effect;

(3) crystal form I, II, VII of the compound represented by formula (1) according to the present invention or a combination thereof has good physicochemical property, stable quality, high content and purity, and stable particle size, and therefore is easy for a large scale of industrial production.

Crystal form I, II, VII of the compound represented by formula (1) according to the present invention or a combination thereof is characterized in that the physical properties, e.g., stability, solubility, hygroscopicity and dissolution rate, appropriate for clinical and therapeutic dosage forms; and also in that the physical properties, e.g., crystal morphology, compressibility, particle sizes and hardness, suitable for manufacture of solid dosage forms. The above properties can be determined with the technologies well known in the art such as X-ray diffraction, microscopy, IR spectroscopy, thermal analysis and hygroscopicity analysis.

Polymorphic forms of the compound are known to affect the solubility, dissolution rate, bioavailability, chemical and physical stability, flowability, fractability, and compressibility of the compound as well as the safety and efficacy of drug products based on the compound (see, e.g., Knapman, Modern Drug Discovery, 2000, 3(2): 53). Thus, it becomes important to produce and market the pure drug in its most thermodynamically stable polymorph and substantially free of other polymorphs.

The crystal form of a compound with optimal physical and chemical properties will advance the development of the active compound as pharmaceuticals. The most useful of such physical and chemical properties include: easy and reproducible preparation, crystallinity, non-hygroscopicity, aqueous solubility, stability to visible and ultraviolet light, low rate of degradation under accelerated stability conditions of temperature and humidity, low rate of isomerization between isomeric forms, and safety for long-term administration to humans. Therefore, it is necessary to show the advantages of crystal forms in the examples.

Crystal form I, II, VII of the compound represented by formula (1) according to the present invention or a combination thereof has storage stability, suitable crystalline shape (crystal morphology), compressibility, flowability, non-sticking, density, particle size stability, the dissolution property and the like that are advantageous for preparation, formulation, use in the formulation and biological availability of the compound represented by formula (1).

Crystal forms I, II, III, IV, V, VI, VII, VIII and amorphous form of the compound represented by formula (1) described in the present invention can be converted each other in a certain condition, and the present invention further provides a conversion relation among crystal form I, crystal form II, crystal form III, crystal form IV, crystal form V, crystal form VI, crystal form VII, crystal form VIII and amorphous form.

Amorphous form is slurry-washed in anhydrous acetonitrile or recrystallized in tetrahydrofuran to produce crystal form I;
Amorphous form is slurry-washed in methanol to produce crystal form II;
Amorphous form is slurry-washed in a mixed solution of acetonitrile and water in a ratio of 1:1-4:1 at 0-70° C. to produce crystal form III;
Amorphous form is slurry-washed in a mixed solution of acetonitrile and water in a ratio of 9:1 at 70-90° C. to produce crystal form IV;
Amorphous form is slurry-washed in isopropyl acetate to produce crystal form VIII;
Crystal form II is slurry-washed in anhydrous acetonitrile to produce crystal form I;
Crystal form III is dried in vacuum to produce crystal form VII;
Crystal form VII is recrystallized in methanol to produce crystal form II;
Crystal forms V, VI and VIII are dried to produce the amorphous form.

Figure 1:
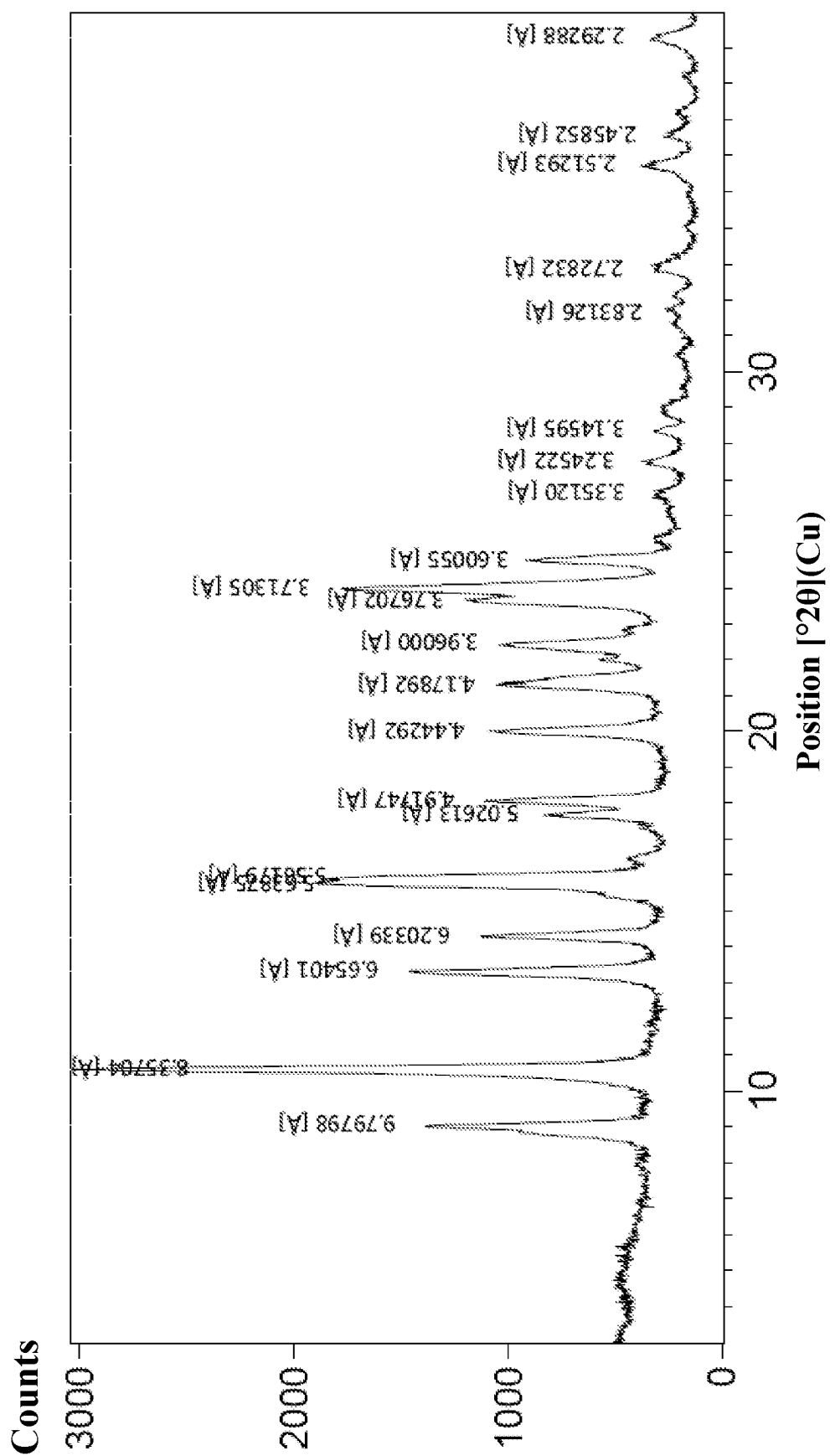
FIG. 1: the XRPD spectrum for crystal form I of the compound represented by formula (1)

The slurry-washing according to the present invention means washing a large amount of solid with a small amount of solvent under stirring.

The lower alcohol according to the present invention means an alcohol containing 1-6 carbon atoms, including methanol, ethanol, propanol, isopropanol, butanol, iso-butanol, n-butanol, pentanol, hexanol and the like.

DETAILED DESCRIPTION OF THE PRESENT INVENTION

The present invention will be described in details by the following embodiments in form of Examples. However, it should be understood that the scope of the present invention is not limited by the following Examples, and all of the technical solutions accomplished based on the above contents of the present invention belong to the scope of the present invention.

Example 1: Preparation of an Amorphous Form of (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydro-tetracene-2-carboxamide According to the preparation process disclosed in the patent application WO2013013505A1, 8 g of (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide was synthesized. The content of the crude product was 84.8%.

8 g of the crude product was dissolved in 1.5 L of water. Trifluoroacetic acid was added to adjust the pH to 2-4. After dissolution, ammonia water was added to adjust the pH to 6.5-7.5. After loading, the preparative separation was carried out with (1‰TFA/water)/acetonitrile (6%) system. The product-containing fraction was collected. The aqueous phase was adjusted with an aqueous sodium hydroxide solution to the pH of 7.5-8.5. The aqueous phase was kept at a temperature of 25-30° C., and extracted with dichloromethane for three times. The dichloromethane phases were combined. The combined dichloromethane phase was concentrated, and dropwise added to n-heptane. The mixture was cooled to a temperature of 0-5° C., stirred for 10-30 min, and filtered by suction to produce 3.17 g of the compound (having a content of 87.7% and a purity of 96.2%).

Molecular formula: $C_{29}H_{36}N_4O_7$
$^1$H-NMR (CD$_3$OD, 400 MHz) δ: 8.48 (s, 1H), 4.54 (brs, 2H), 4.22 (s, 1H), 3.65 (brs, 4H), 3.46 (m, 1H), 3.35 (s, 6H), 3.25 (m, 1H), 3.10 (s, 3H), 3.05 (s, 1H), 3.00 (s, 3H), 2.60 (m, 1H), 2.37 (m, 1H), 1.87-1.97 (m, 2H), 1.68 (m, 1H), 1.07 (m, 1H), 0.78 (m, 1H).

In order to prepare the amorphous form of (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide having a high content, the following processes were attempted:

Crystal form II of the compound represented by formula (1) (having a content of 95.6%) was dissolved in an appropriate amount of dichloromethane, and dropwise added to the n-heptane system at a temperature of 0-5° C. The mixture was stirred for 30 min, and filtered by suction. The resulting solid was dried in vacuum to produce the amorphous form of the compound represented by formula (1) (having a content of 93.3%).

Crystal form II of the compound represented by formula (1) (having a content of 97.0%) was dissolved in an appropriate amount of dichloromethane, and dropwise added to the n-heptane system at a temperature of 0-5° C. The mixture was stirred for 30 min, and filtered by suction. The resulting solid was dried in vacuum to produce the amorphous form of the compound represented by formula (1) (having a content of 93.9%).

Crystal form II of the compound represented by formula (1) (having a content of 98.4%) was dissolved in an appropriate amount of dichloromethane, and dropwise added to the n-heptane system at a temperature of 0-5° C. The mixture was stirred for 30 min, and filtered by suction. The resulting solid was dried in vacuum to produce the amorphous form of the compound represented by formula (1) (having a content of 97.1%).

Figure 13:
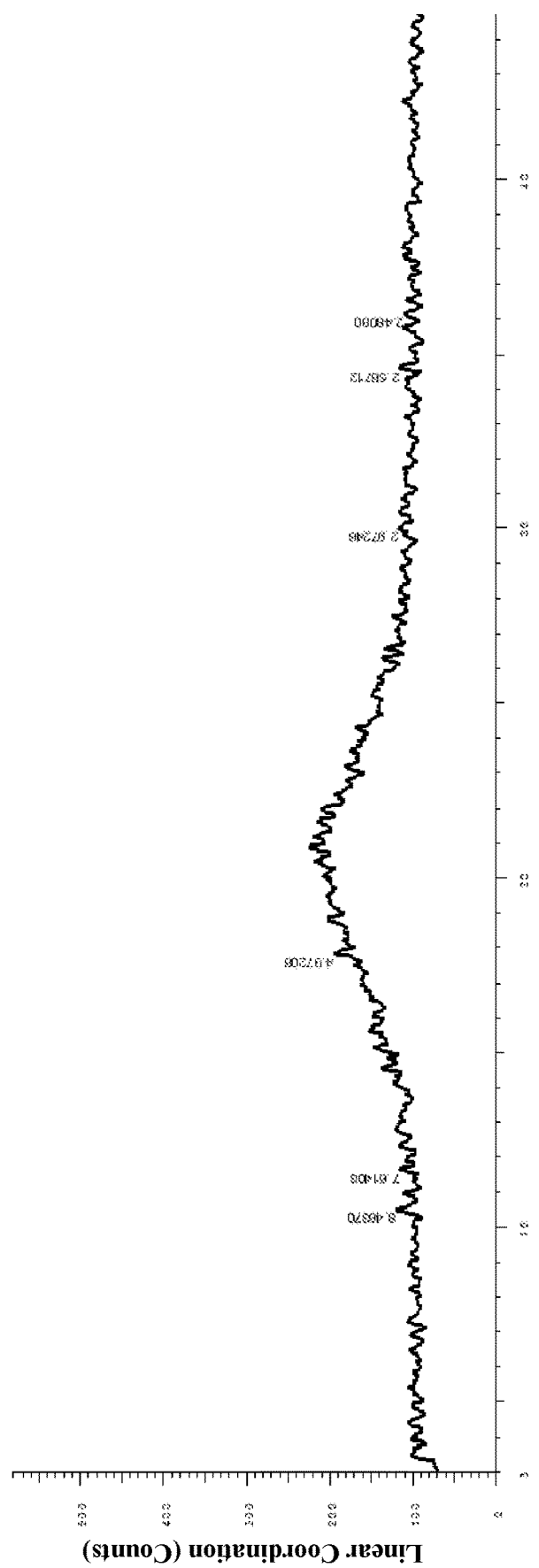
FIG. 13: the XRPD spectrum for amorphous form of the compound represented by formula (1)
Figure 14:
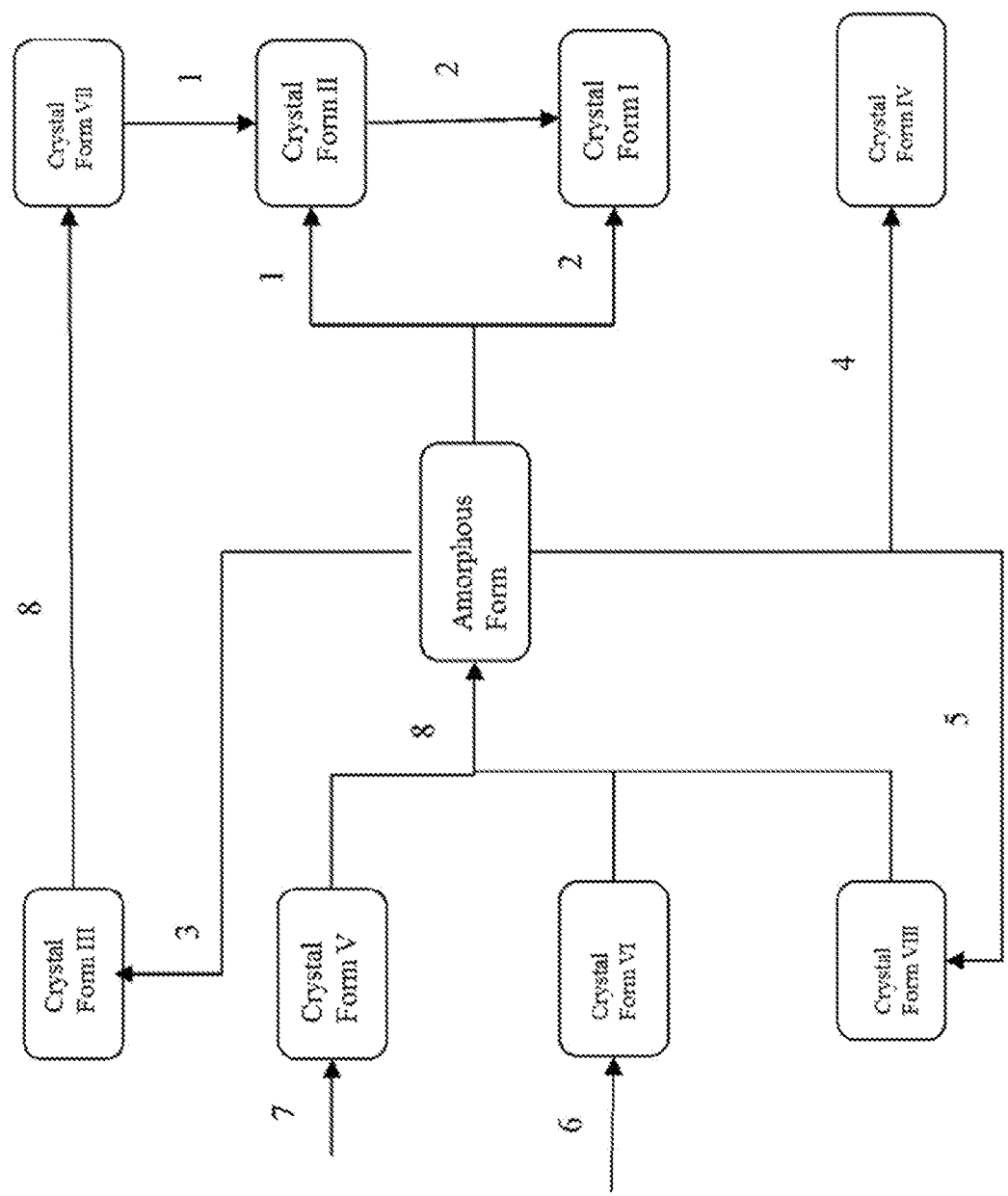
FIG. 14: the conversion relation among crystal form I, crystal form II, crystal form III, crystal form IV, crystal form V, crystal form VI, crystal form VII, crystal form VIII and amorphous form of the compound represented by formula (1), wherein:
1. Slurry-washing in methanol or slurry-washing in a mixed solution of methanol and water (1:1-9:1, v/v);
2. Slurry-washing in acetonitrile or tetrahydrofuran;
3. Slurry-washing in a mixed solution of acetonitrile and water in a ratio of 1:1-4:1;
4. Slurry-washing in a mixed solution of acetonitrile and water in a ratio 9:1;
5. Slurry-washing in isopropyl acetate;
6. Crystallization with slow volatilization of chloroform solution or under the induction of polyvinyl acetate, polyphenylene sulfide, 1,3-dimethylimidazoline mesylate or 1,3-dimethylimidazoline perchlorate in the chloroform solution,
7. Slow volatilization of a mixed solution of tetrahydrofuran and isopropyl acetate (1:1, v/v); and
8. Drying under heat.

The solid was characterized with XPRD as an amorphous form, as shown in FIG. 13.

Example 2: Preparation of Crystal Form I of (4S, 4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide 0.5 g of the amorphous form of the compound represented by formula (1) prepared in Example 1 (having a content of 87.7%, and a purity of 96.2%) was placed in 5 mL of acetonitrile or 2 mL of THF. The mixture was heated to 55° C. and stirred for 0.5 h, and filtered. The obtained solid was placed in a vacuum drying oven and dried in vacuum at 50° C. for 12 h to produce crystal form I having a content of 97.0%, and a purity of 98.2%.

Crystal form I had an X-ray powder diffraction (XRPD) spectrum as shown in FIG. 1, in which the main parameters were as follows:

| 2θ angles (°) | d value (Å) | Strength (%) |
| --- | --- | --- |
| 9.025765 | 9.79798 | 38.74 |
| 10.586120 | 8.35704 | 100.00 |
| 13.306510 | 6.65401 | 43.61 |
| 14.277980 | 6.20339 | 31.16 |
| 15.716330 | 5.63875 | 55.34 |
| 15.935210 | 5.56179 | 53.43 |
| 17.646390 | 5.02613 | 19.96 |
| 18.039520 | 4.91747 | 31.42 |
| 19.985140 | 4.44292 | 30.34 |
| 21.261890 | 4.17892 | 28.80 |
| 21.452190 | 3.96000 | 28.54 |
| 23.618520 | 3.76702 | 35.07 |
| 23.966900 | 3.71305 | 58.77 |
| 24.727390 | 3.60055 | 24.17 |
| 26.599820 | 3.35120 | 4.21 |
| 27.485250 | 3.24522 | 6.23 |
| 28.370430 | 3.14595 | 4.91 |
| 31.601690 | 2.83126 | 2.64 |
| 32.827100 | 2.72832 | 6.25 |
| 35.731580 | 2.51293 | 8.09 |
| 36.550010 | 2.45852 | 4.56 |
| 39.294720 | 2.29288 | 6.57 |

Figure 2:
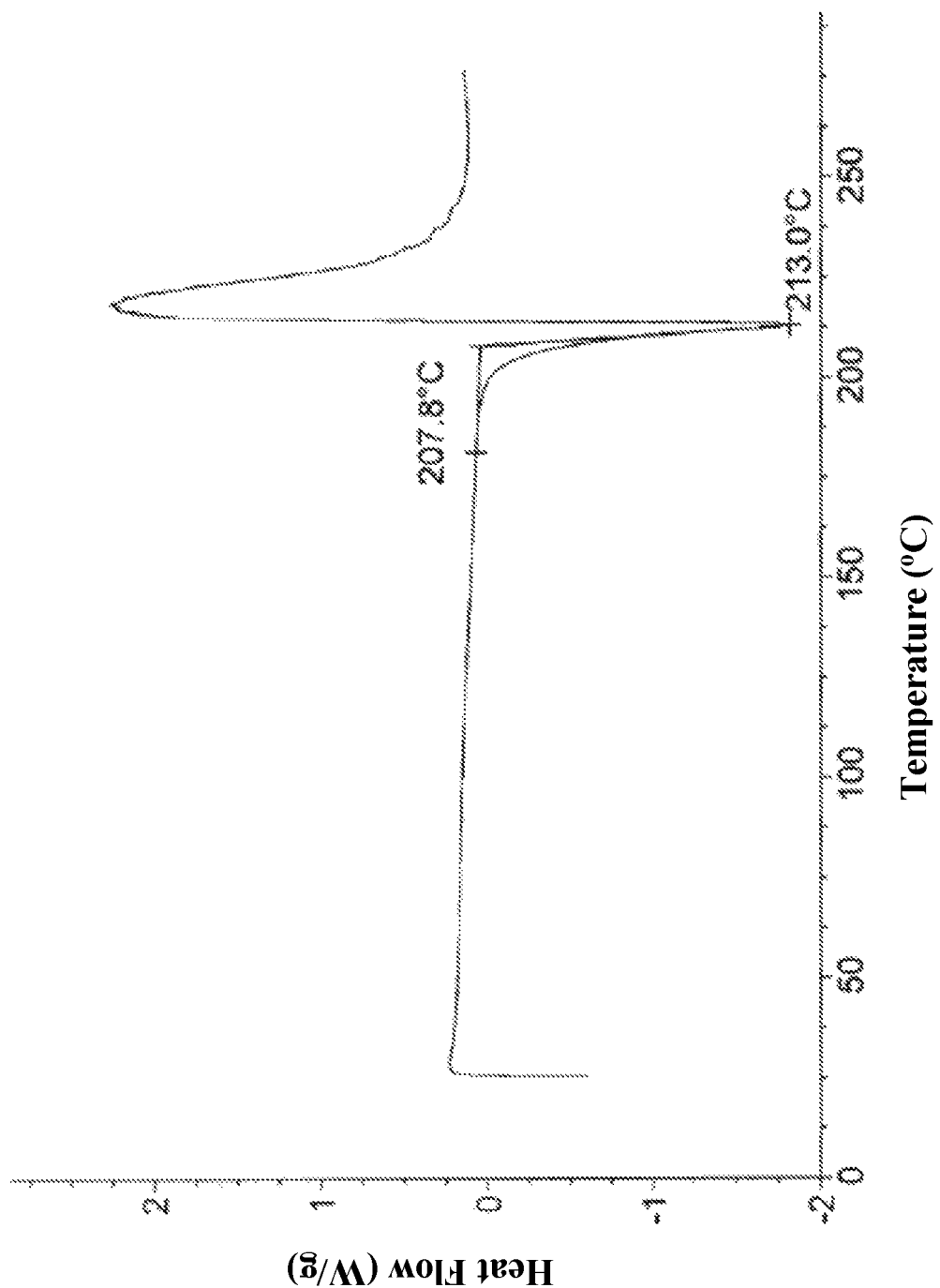
FIG. 2: the DSC curve for crystal form I of the compound represented by formula (1)

Crystal form I of the compound represented by formula (1) had a DSC curve as shown in FIG. 2.

Example 3: Preparation of Crystal Form II of (4S, 4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide Method 1: 1.0 g of the amorphous form of the compound represented by formula (1) prepared in Example 1 (having a content of 87.7%, and a purity of 96.2%) was dissolved in 10 mL of methanol. The mixture was stirred at 55° C. for 1-2 h, and filtered. The obtained solid was placed in a vacuum drying oven, and dried in vacuum at 50° C. for 12 h to produce crystal form II having a content of 94.5%, and a purity of 96.4%.

Method 2: 1.0 g of the amorphous form of the compound represented by formula (1) prepared in Example 1 (having a content of 87.7%, and a purity of 96.2%), after several purifications, was dissolved in 10 mL of methanol. The mixture was stirred at 55° C. for 1-2 h, and filtered. The obtained solid was placed in a vacuum drying oven, and dried in vacuum at 50° C. for 12 h to produce crystal form II having a content of 98.4%.

Method 3: 15 mg of the obtained compound represented by formula (1) was placed in a 3 mL vial. The vial was placed in a 20 mL carboy. The carboy contains 4 mL of methanol. After being placed at room temperature for 10 days, the solid was crystal form II.

Method 4: 15 mg of the obtained compound represented by formula (1) was placed in a 3 mL vial and dissolved in 0.6 mL of THF. The vial was placed in a 20 mL carboy. The carboy contains 4 mL of n-heptane. After being placed at room temperature for 4 days, a solid separated from the mixture. The mixture was filtered to produce crystal form II.

Figure 3:
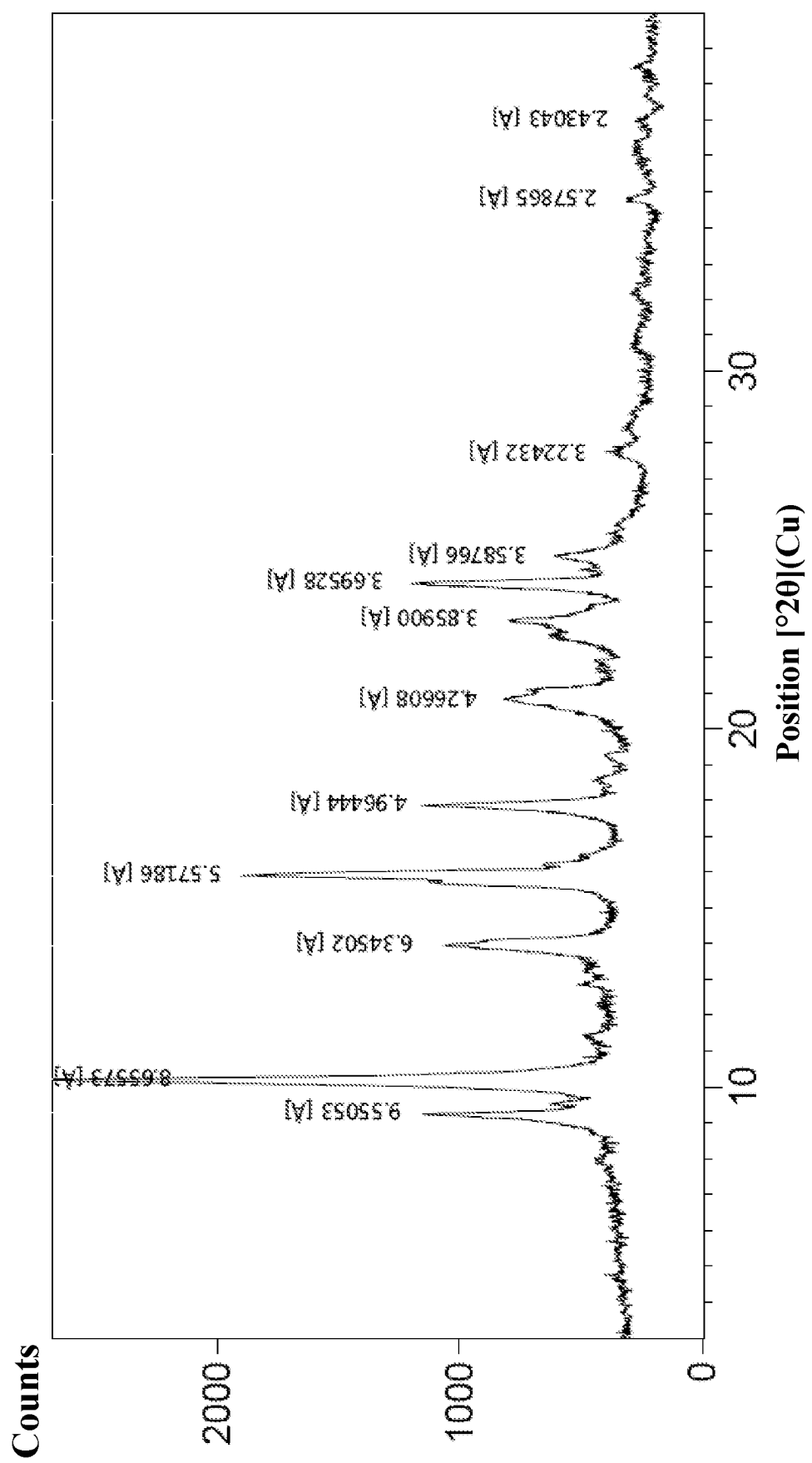
FIG. 3: the XRPD spectrum for crystal form II of the compound represented by formula (1)
Figure 4:
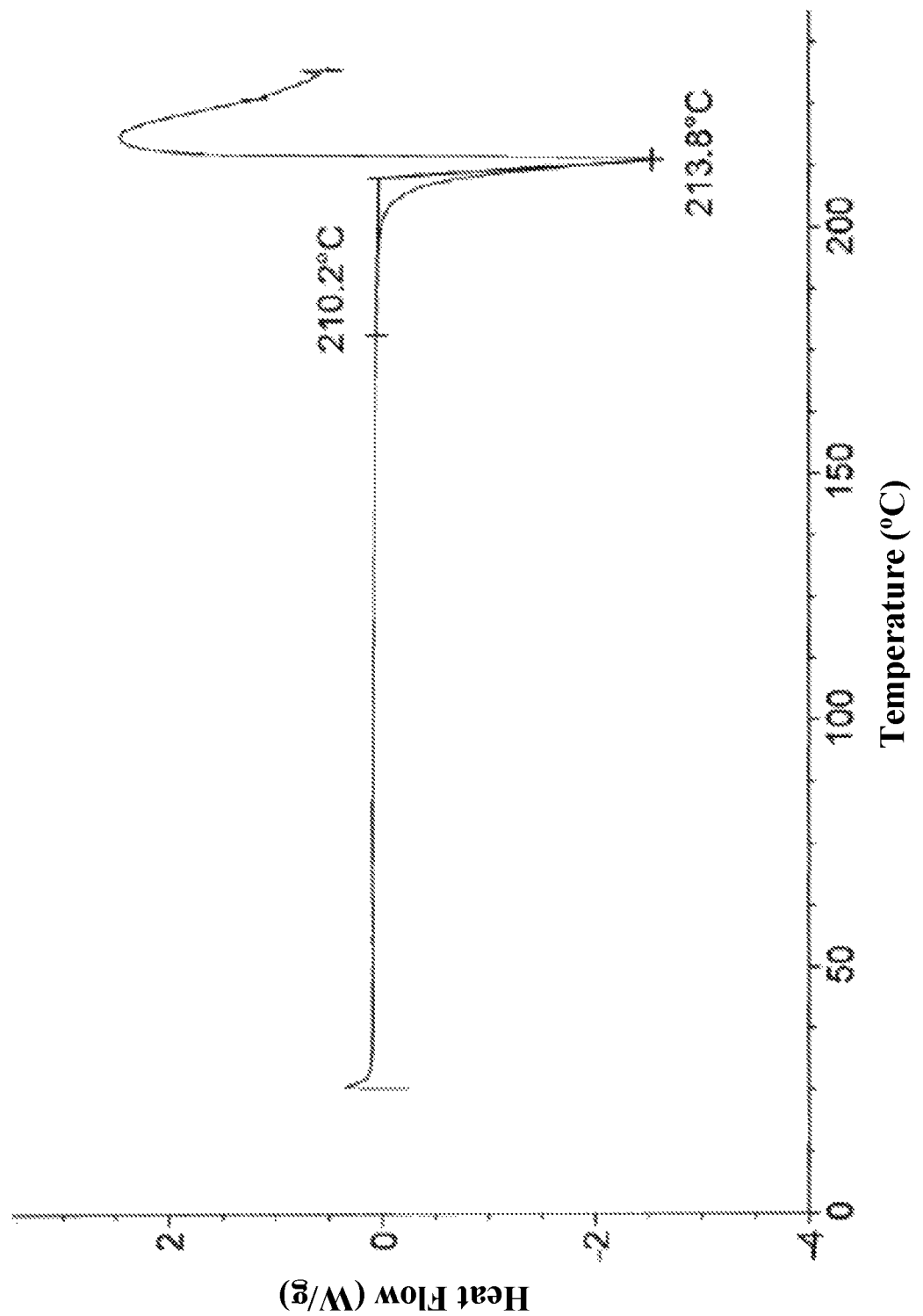
FIG. 4: the DSC curve for crystal form II of the compound represented by formula (1)

Crystal form II had an X-ray powder diffraction (XRPD) spectrum as shown in FIG. 3, in which the main parameters were as follows:

| 2θ angles (°) | d value (Å) | Strength (%) |
| --- | --- | --- |
| 9.260124 | 9.55053 | 32.36 |
| 10.219830 | 8.65573 | 100.00 |
| 13.957680 | 6.34502 | 30.22 |
| 15.906220 | 5.57186 | 67.00 |
| 17.867450 | 4.96444 | 33.45 |
| 20.822590 | 4.26608 | 21.68 |
| 23.047770 | 3.85900 | 22.73 |
| 24.083840 | 3.69528 | 40.93 |
| 24.817680 | 3.58766 | 14.67 |
| 27.666960 | 3.22432 | 4.69 |
| 34.791430 | 2.57865 | 4.46 |
| 36.987580 | 2.43043 | 2.36 |

Example 4: Preparation of Crystal Form III of (4S, 4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide (as Acetonitrile Solvate)

Method 1: 500 mg of the amorphous form of the compound represented by formula (1) prepared in Example 1 (having a content of 87.7%, and a purity of 96.2%) was placed in a mixed solution of acetonitrile and water (1:1). The mixture was stirred at 5° C. for 2 h, and filtered to produce crystal form III having a content of 90.1%, and a purity of 97.7%. The data for investigating the stability was mentioned as above.

Method 2: 16.1 mg of the amorphous form of the compound represented by formula (1) prepared in Example 1 (having a content of 97.1%) was placed in a mixed solution of 0.15 mL of acetonitrile and 0.15 mL of water. The mixture was stirred at 5° C. for 2 h, and filtered to produce crystal form III.

Figure 5:
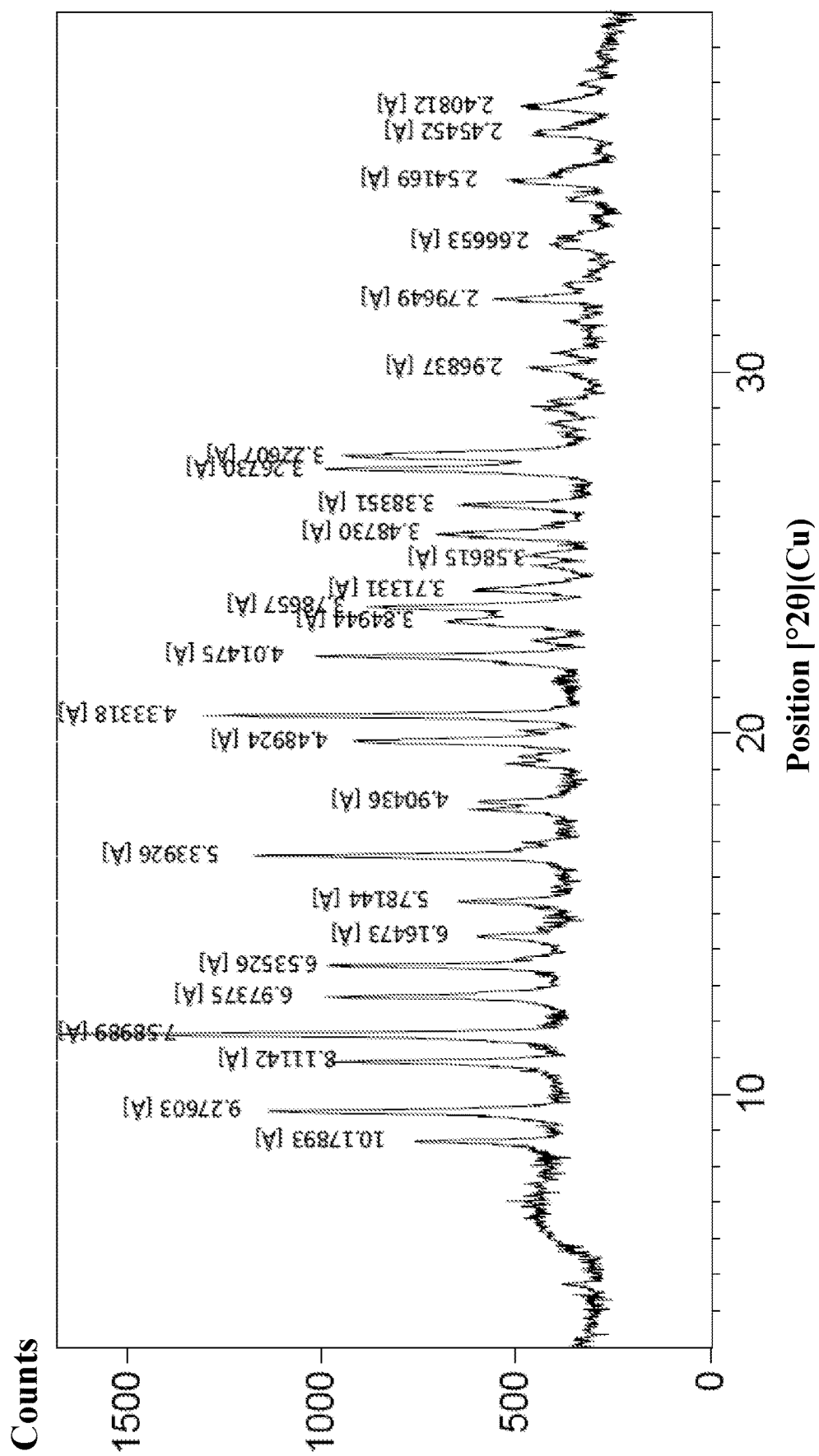
FIG. 5: the XRPD spectrum for crystal form III of the compound represented by formula (1)
Figure 6:
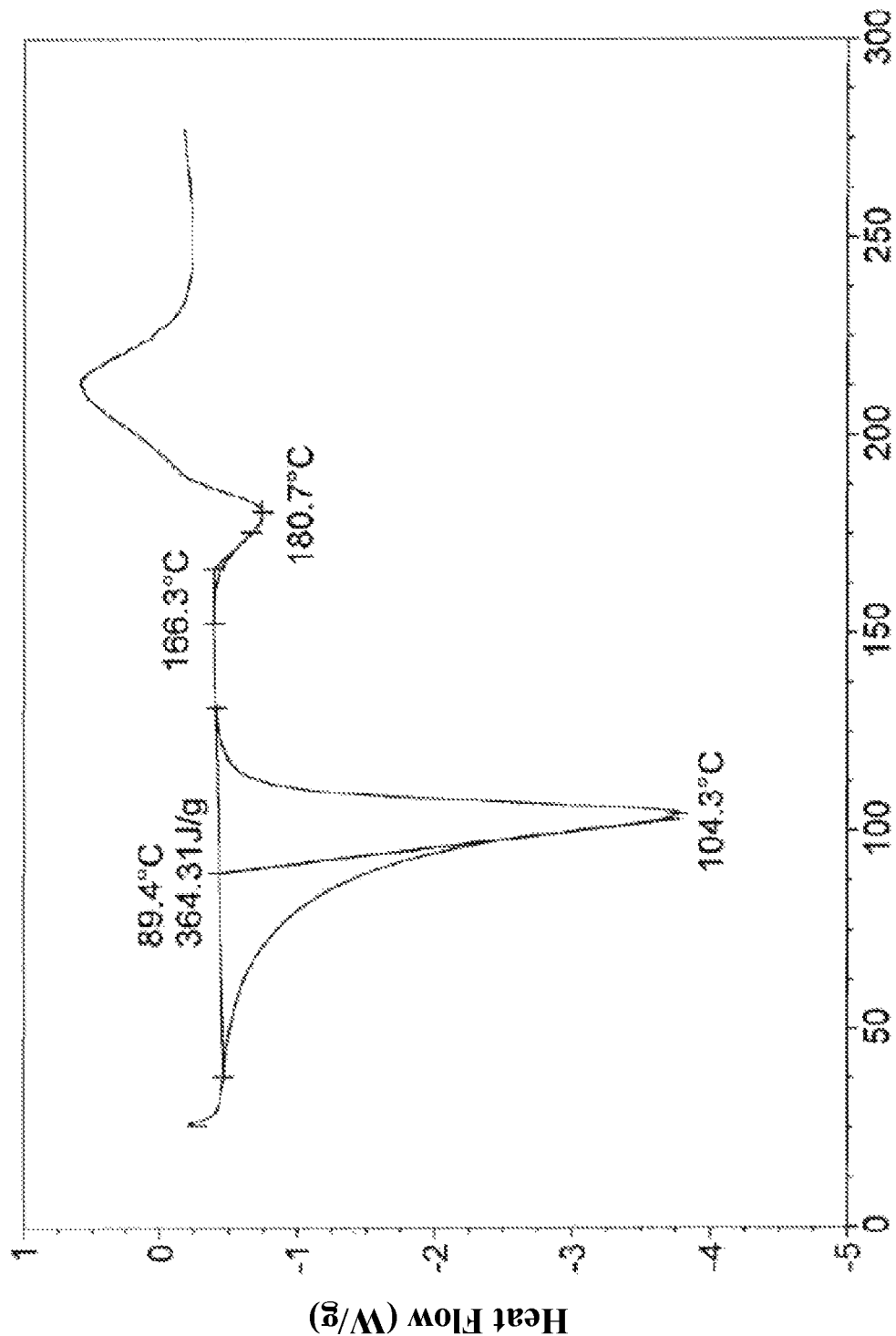
FIG. 6: the DSC curve for crystal form III of the compound represented by formula (1)

Crystal form III had an X-ray powder diffraction (XRPD) spectrum as shown in FIG. 5, and a DSC curve as shown in FIG. 6, in which the main parameters were as follows:

| 2θ angles (°) | d value (Å) | Strength (%) |
|---|---|---|
| 8.687313 | 10.17893 | 27.52 |
| 9.534775 | 9.27603 | 57.43 |
| 10.907640 | 8.11142 | 39.04 |
| 11.659660 | 7.58989 | 100.00 |
| 12.693860 | 6.97375 | 48.44 |
| 13.549430 | 6.53526 | 43.82 |
| 14.368000 | 6.16473 | 17.17 |
| 15.326080 | 5.78144 | 21.57 |
| 16.603930 | 5.33926 | 64.78 |
| 18.088170 | 4.90436 | 18.77 |
| 19.776820 | 4.48924 | 44.02 |
| 20.496670 | 4.33318 | 76.31 |
| 22.142080 | 4.01475 | 53.89 |
| 23.105800 | 3.84944 | 27.66 |
| 23.494860 | 3.78657 | 41.85 |
| 23.965170 | 3.71331 | 21.43 |
| 24.828240 | 3.58615 | 5.35 |
| 25.543780 | 3.48730 | 27.49 |
| 26.341220 | 3.38351 | 24.53 |
| 27.295890 | 3.26730 | 51.68 |
| 27.651590 | 3.22607 | 47.77 |
| 30.106550 | 2.96837 | 11.96 |
| 32.005070 | 2.79649 | 17.76 |
| 33.610130 | 2.66653 | 8.05 |
| 35.313900 | 2.54169 | 18.90 |
| 36.611660 | 2.45452 | 14.25 |
| 37.342910 | 2.40812 | 15.87 |

Example 5: Preparation of Crystal Form IV of (4S, 4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide 15 mg of the amorphous form of the compound represented by formula (1) prepared in Example 1 was placed in a mixed solution of 0.9 mL of acetonitrile and 0.1 mL of water. The mixture was stirred at 80° C. for 2 h, and filtered to produce crystal form IV. Crystal form IV was unstable, resulting in a bad repeatability.

Figure 7:
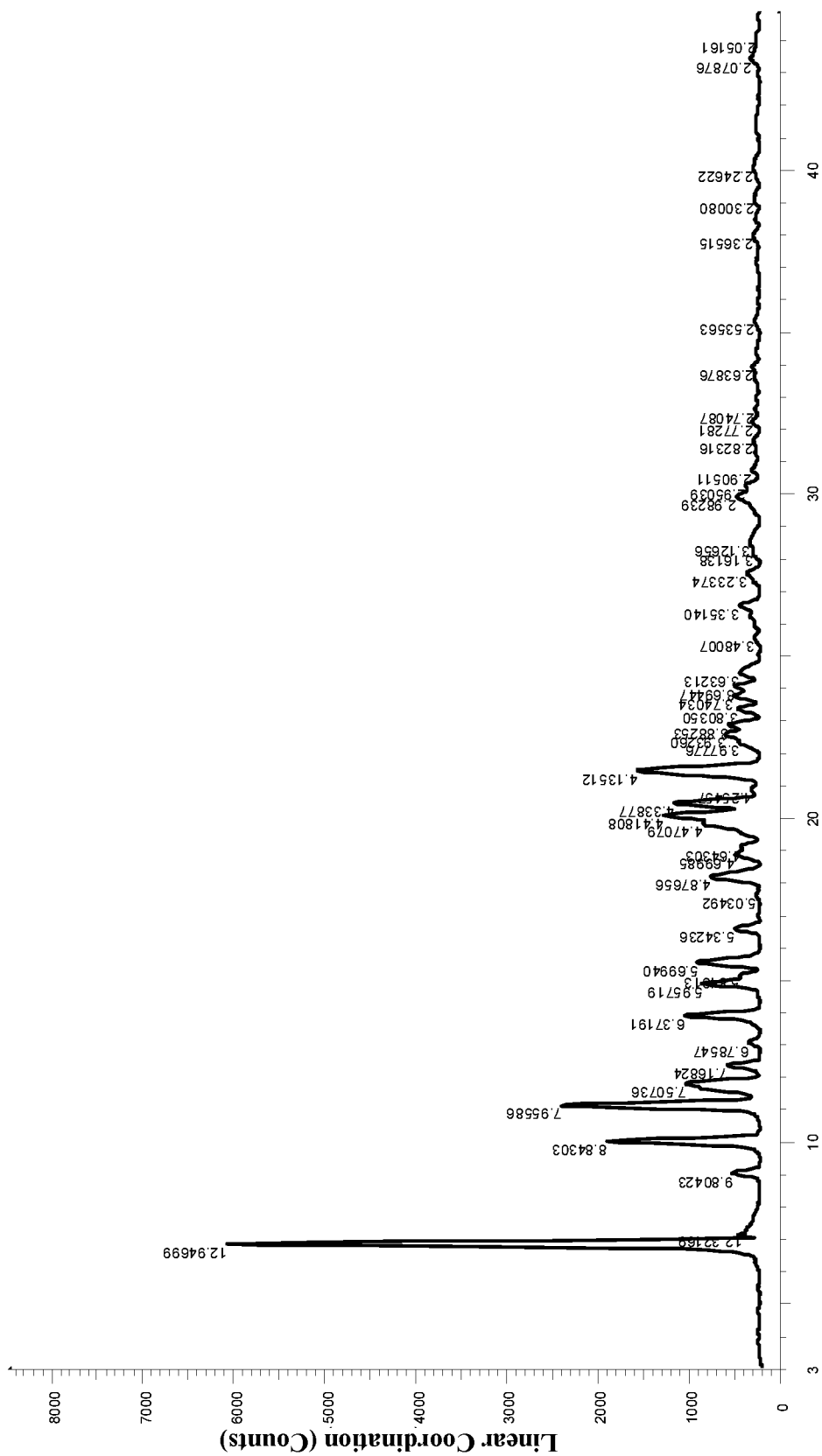
FIG. 7: the XRPD spectrum for crystal form IV of the compound represented by formula (1)

Crystal form IV had an X-ray powder diffraction (XRPD) spectrum as shown in FIG. 7, in which the main parameters were as follows:

| 2θ angles (°) | d value (Å) | Strength (%) |
|---|---|---|
| 6.822 | 12.94699 | 100.0 |
| 7.168 | 12.32169 | 6.5 |
| 9.013 | 9.80423 | 8.3 |
| 9.995 | 8.84303 | 31.0 |
| 11.112 | 7.95586 | 39.2 |
| 11.779 | 7.50736 | 16.7 |
| 12.338 | 7.16824 | 9.3 |
| 13.037 | 6.78547 | 5.3 |
| 13.887 | 6.37191 | 16.8 |
| 14.859 | 5.95719 | 13.8 |
| 15.143 | 5.84613 | 7.1 |
| 15.535 | 5.69940 | 14.6 |
| 16.580 | 5.34236 | 7.8 |
| 17.601 | 5.03492 | 3.9 |
| 18.177 | 4.87656 | 12.4 |
| 18.867 | 4.69985 | 7.8 |
| 19.100 | 4.64303 | 6.7 |
| 19.843 | 4.47079 | 13.6 |
| 20.082 | 4.41808 | 20.8 |
| 20.453 | 4.33877 | 18.9 |
| 20.862 | 4.25457 | 4.9 |
| 21.472 | 4.13512 | 25.6 |
| 22.332 | 3.97776 | 7.1 |
| 22.592 | 3.93260 | 9.6 |
| 22.887 | 3.88253 | 8.9 |
| 23.369 | 3.80350 | 7.3 |
| 23.770 | 3.74034 | 8.1 |
| 24.069 | 3.69447 | 7.8 |
| 24.488 | 3.63213 | 7.0 |
| 25.576 | 3.48007 | 4.4 |
| 26.576 | 3.35140 | 7.0 |
| 27.561 | 3.23374 | 5.7 |
| 28.205 | 3.16138 | 4.6 |
| 28.526 | 3.12656 | 5.2 |
| 29.936 | 2.98239 | 7.5 |
| 30.269 | 2.95039 | 5.8 |
| 30.752 | 2.90511 | 4.9 |
| 31.668 | 2.82316 | 4.5 |
| 32.258 | 2.77281 | 4.7 |
| 32.645 | 2.74087 | 4.2 |
| 33.946 | 2.63876 | 4.7 |
| 35.371 | 2.53563 | 4.4 |
| 38.014 | 2.36515 | 4.7 |
| 39.120 | 2.30080 | 4.3 |
| 40.111 | 2.24622 | 4.6 |
| 43.500 | 2.07876 | 4.9 |
| 44.106 | 2.05161 | 4.1 |

Example 6: Preparation of Crystal Form V of (4S, 4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide (as Isopropyl Acetate Solvate)

Method 1: 14.8 mg of the compound represented by formula (1) prepared in Example 1 was dissolved in 0.7 mL of THF and 0.7 mL of isopropyl acetate. The solvent slowly volatilized at 5° C. or at room temperature, and a solid separated from the mixture. The mixture was filtered to produce crystal form V.

Method 2: 15 mg of the compound represented by formula (1) prepared in Example 1 was dissolved in 1.0 mL of THF. Then 4 mL of isopropyl acetate was dropwise added, and a solid separated from the mixture. The mixture was filtered to produce the crystal form.

Figure 8:
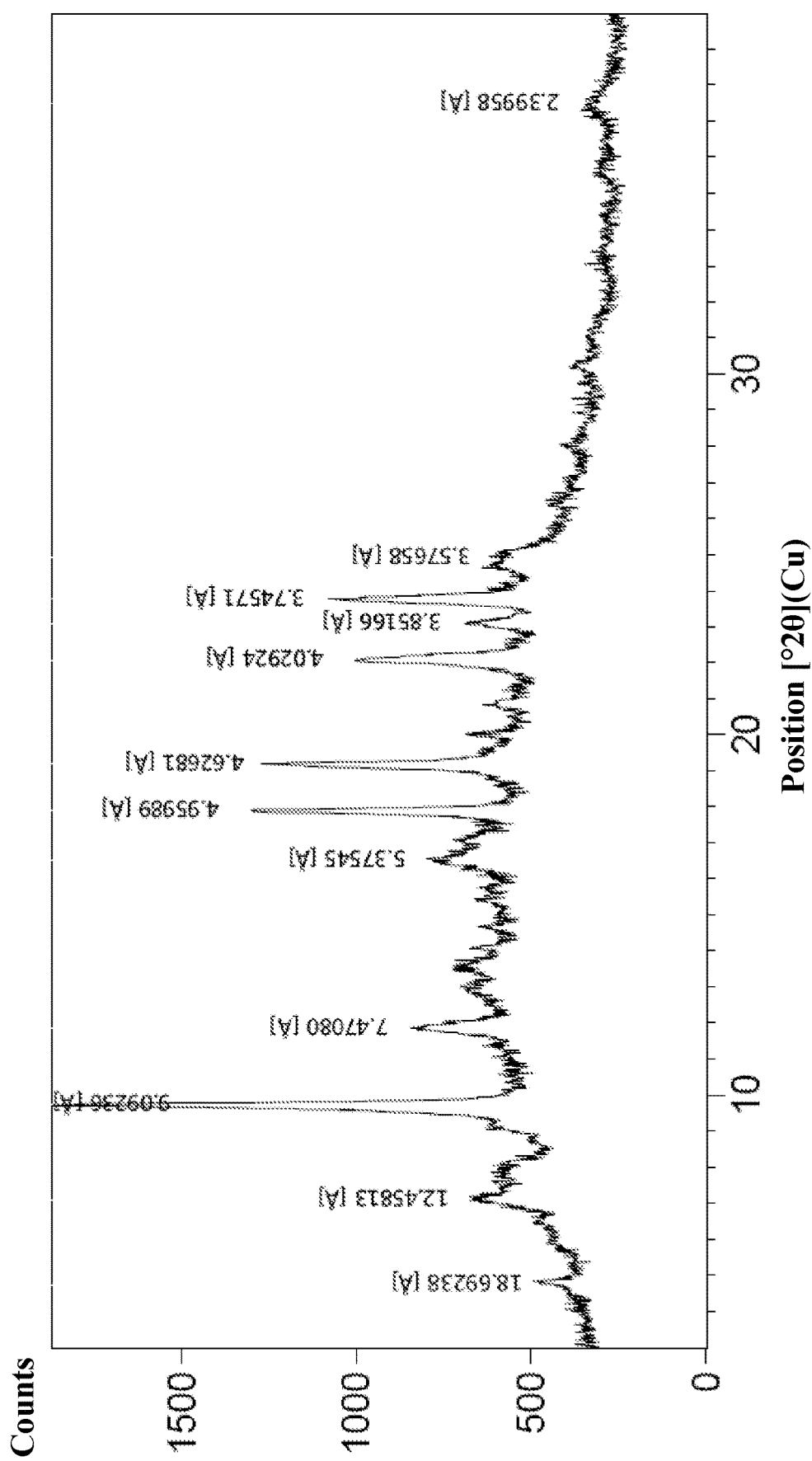
FIG. 8: the XRPD spectrum for crystal form V of the compound represented by formula (1)

Crystal form V had an X-ray powder diffraction (XRPD) spectrum as shown in FIG. 8, in which the main parameters were as follows:

| 2θ angles (°) | d value (Å) | Strength (%) |
|---|---|---|
| 4.727485 | 18.69238 | 4.86 |
| 7.095715 | 12.45813 | 16.14 |
| 9.727849 | 9.09236 | 100.00 |
| 11.846180 | 7.47080 | 17.17 |
| 16.491390 | 5.37545 | 14.44 |
| 17.883960 | 4.95989 | 56.77 |
| 19.183180 | 4.62681 | 53.32 |
| 22.061500 | 4.02924 | 39.42 |
| 23.092320 | 3.85166 | 15.52 |
| 23.754860 | 3.74571 | 45.79 |

| 2θ angles (°) | d value (Å) | Strength (%) |
|---|---|---|
| 24.895740 | 3.57658 | 11.30 |
| 37.480630 | 2.39958 | 4.29 |

Example 7: Preparation of Crystal Form VI of (4S, 4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide (as Chloroform Solvate)

Method 1: 15 mg of the compound represented by formula (1) prepared in Example 1 was dissolved in 0.5 mL of chloroform. The solvent slowly volatilized at room temperature, and a solid separated from the mixture to produce crystal form VI.

Method 2: 16.1 mg of the compound represented by formula (1) prepared in Example 1 was placed in a 3 mL vial, and dissolved in 0.8 mL of chloroform. The vial was placed in a 20 mL carboy, and the carboy contained 4 mL of isopropanol or n-heptane. The mixture was placed at room temperature for 4 days. A solid separated from the mixture to produce crystal form VI.

Method 3: 15 mg of crystal form II of the compound represented by formula (1) prepared in the example was placed in a 3 mL vial, and the vial was placed in a 20 mL carboy. The carboy contained 4 mL of chloroform. The mixture was placed at room temperature for 10 days, and the resulting solid was crystal form VI.

Method 4: 15 mg of the compound represented by formula (1) was placed in a 3 mL vial. 0.5 mL of chloroform was added until dissolved. Then 2.98 mg of polyphenylene sulfide was added. The solvent slowly volatilized at room temperature, and a solid separated from the mixture to produce crystal form VI.

Method 5: 15 mg of the compound represented by formula (1) was placed in a 3 mL vial. 0.5 mL of chloroform was added until dissolved. Then 3 mg of 1,3-dimethylimidazoline mesylate was added. The solvent slowly volatilized at room temperature, and a solid separated from the mixture to produce crystal form VI.

Figure 9:
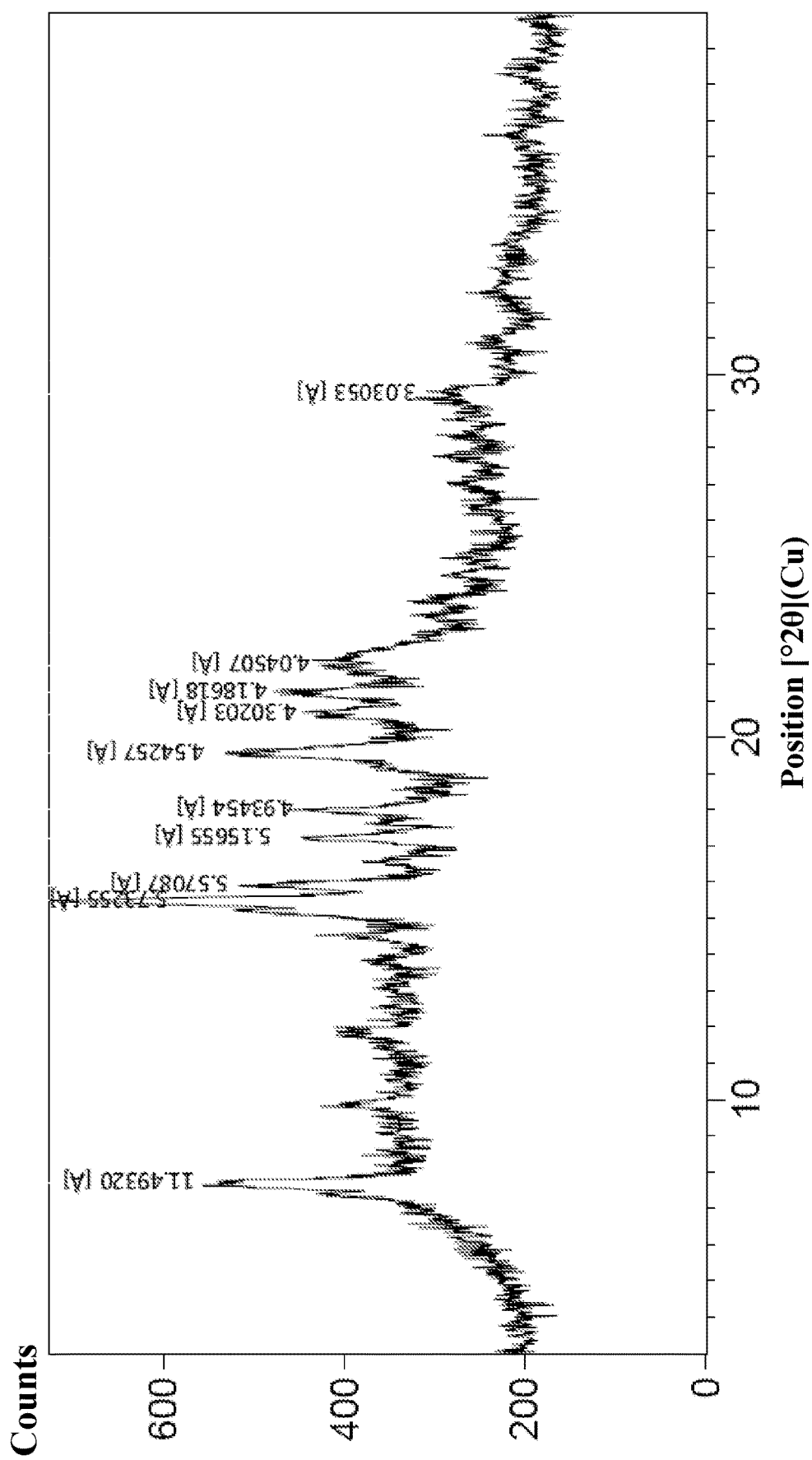
FIG. 9: the XRPD spectrum for crystal form VI of the compound represented by formula (1)

Crystal form VI had an X-ray powder diffraction (XRPD) spectrum as shown in FIG. 9, in which the main parameters were as follows:

| 2θ angles (°) | d value (Å) | Strength (%) |
|---|---|---|
| 7.692313 | 11.49320 | 58.12 |
| 15.457590 | 5.73255 | 100.00 |
| 15.909050 | 5.57087 | 43.32 |
| 17.196630 | 5.15655 | 34.40 |
| 17.976590 | 4.93454 | 29.91 |
| 19.542360 | 4.54257 | 56.79 |
| 20.646680 | 4.30203 | 32.34 |
| 21.224630 | 4.18618 | 40.47 |
| 21.974070 | 4.04507 | 28.99 |
| 29.474920 | 3.03053 | 13.31 |

Example 8: Preparation of Crystal Form VII of (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide Method 1: 16.1 mg of the amorphous form of the compound represented by formula (1) prepared in Example 1 was placed in a mixed solution of 0.15 mL of acetonitrile and 0.15 mL of water. The mixture was stirred at 5° C. for 2 h, filtered, and dried in vacuum to produce crystal form VII.

Method 2: 15 mg of crystal form II of the compound represented by formula (1) prepared in the Examples was placed in a mixed solution of 0.8 mL of acetonitrile and 0.2 mL of water (ACN/H$_2$O, V/V, 4:1). The mixture was reacted at room temperature, filtered, dried in vacuum at 50° C. for 2 h to produce a solid as crystal form VII.

Method 3: crystal form III of the compound represented by formula (1) prepared in the Examples was dried in vacuum to produce crystal form VII.

Figure 10:
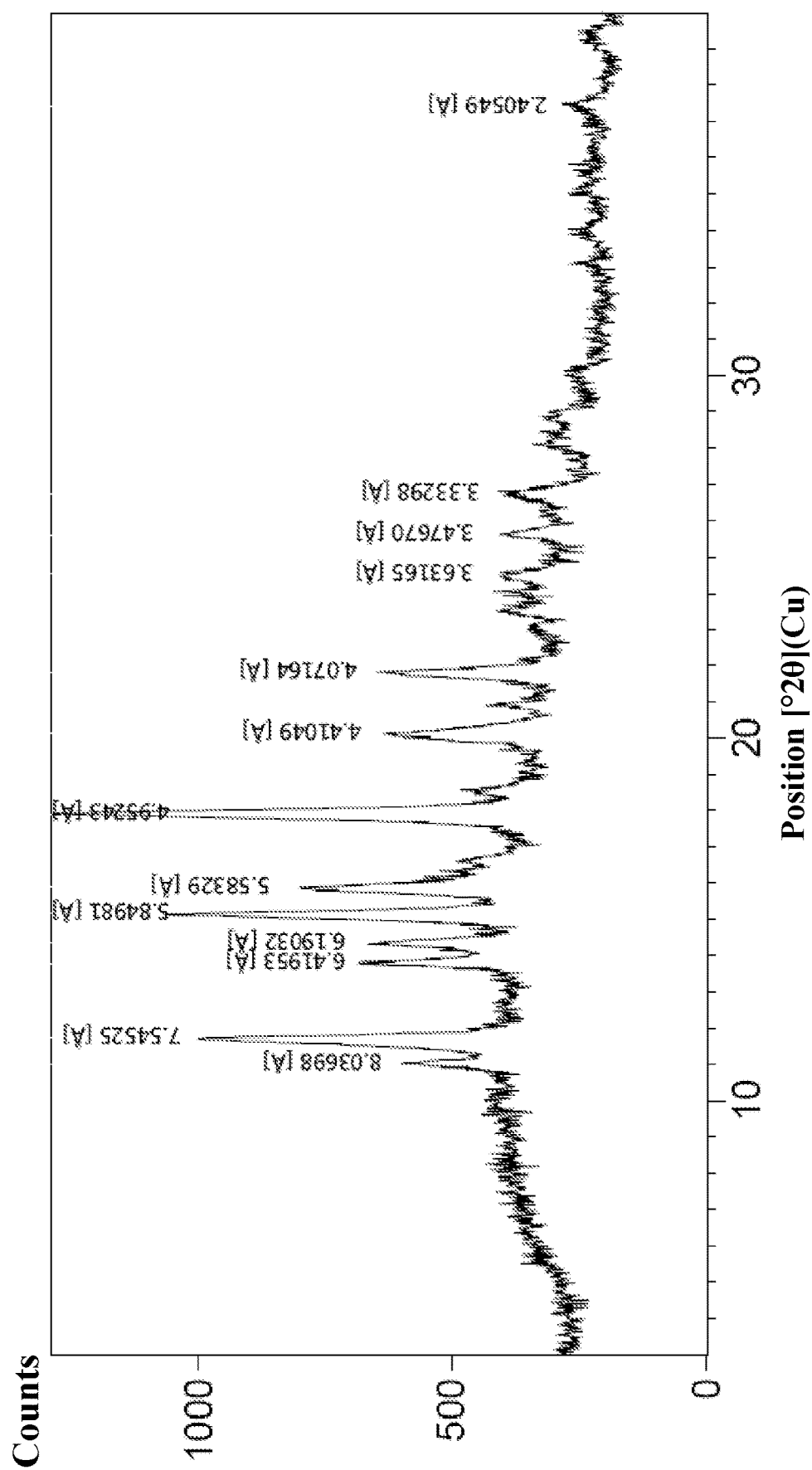
FIG. 10: the XRPD spectrum for crystal form VII of the compound represented by formula (1)
Figure 11:
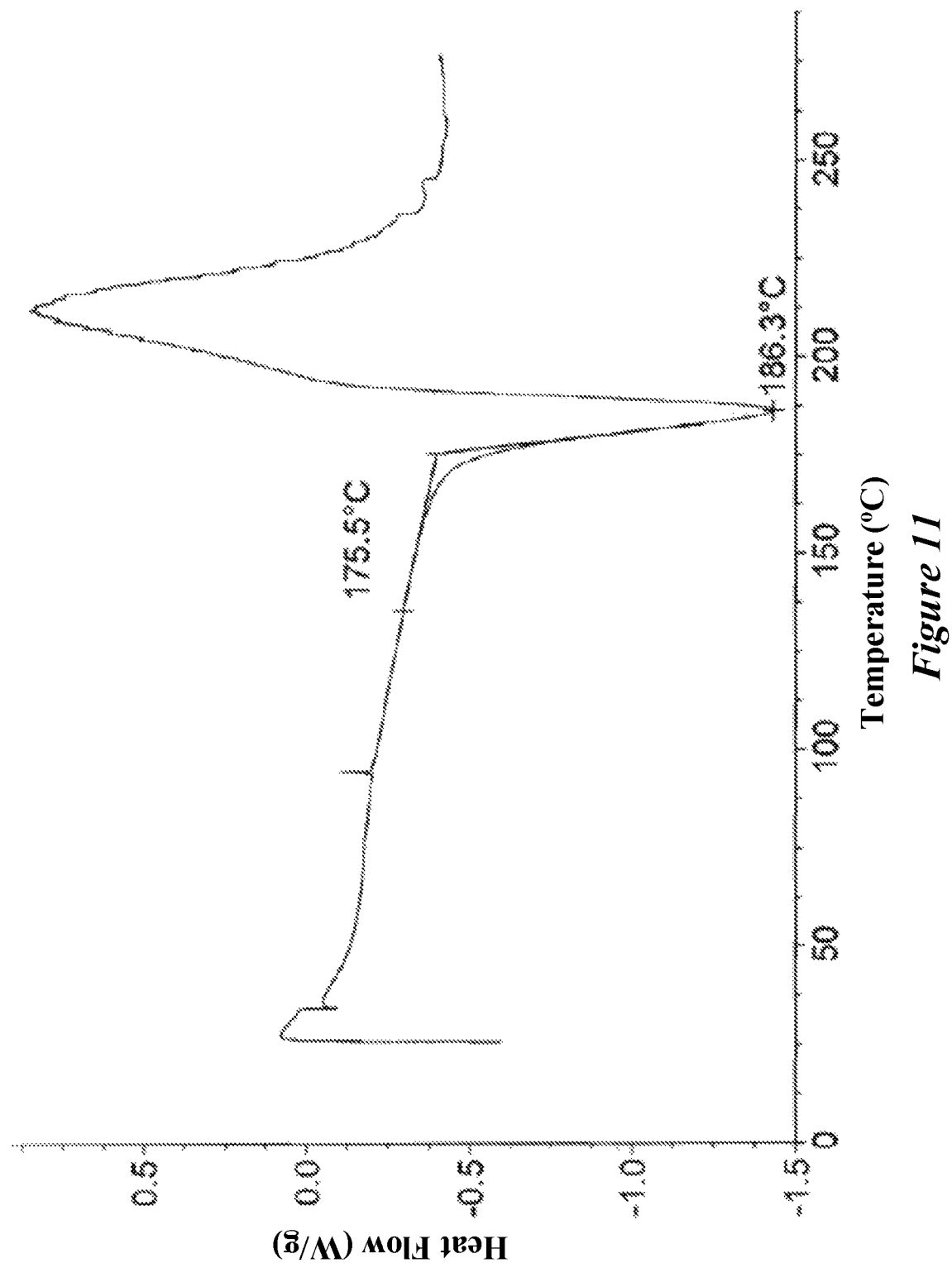
FIG. 11: the DSC curve for crystal form VII of the compound represented by formula (1)

Crystal form VII had an X-ray powder diffraction (XRPD) spectrum as shown in FIG. 10, in which the main parameters were as follows:

| 2θ angles (°) | d value (Å) | Strength (%) |
|---|---|---|
| 11.008970 | 8.03698 | 20.09 |
| 11.728880 | 7.54525 | 62.33 |
| 13.794880 | 6.41953 | 30.30 |
| 14.308280 | 6.19032 | 30.51 |
| 15.145890 | 5.84981 | 69.50 |
| 15.873440 | 5.58329 | 47.53 |
| 17.911120 | 4.95243 | 100.00 |
| 20.133590 | 4.41049 | 32.48 |
| 21.828890 | 4.07164 | 34.86 |
| 24.512310 | 3.63165 | 12.97 |
| 25.622960 | 3.47670 | 14.08 |
| 26.747930 | 3.33298 | 13.74 |
| 37.385250 | 2.40549 | 4.92 |

Example 9: Preparation of Crystal Form VIII of (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide (as Isopropyl Acetate Solvate)

15 mg of the amorphous form of the compound represented by formula (1) prepared in Example 1 was placed in 1 mL of isopropyl acetate. The mixture was stirred at 5° C. for 2 h, filtered to produce a solid as crystal form VIII.

Figure 12:
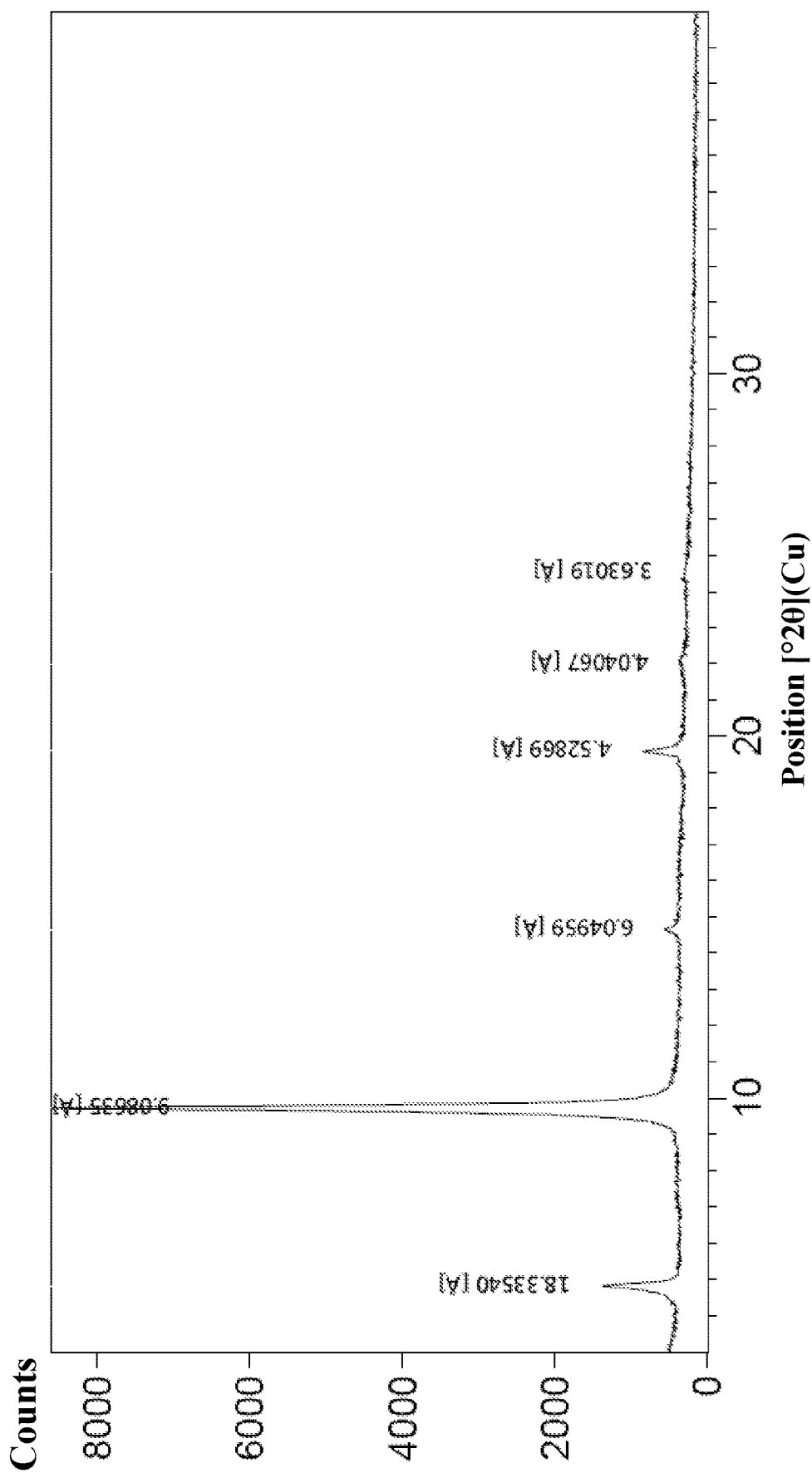
FIG. 12: the XRPD spectrum for crystal form VIII of the compound represented by formula (1)

Crystal form VIII had an X-ray powder diffraction (XRPD) spectrum as shown in FIG. 12, in which the main parameters were as follows:

| 2θ angles (°) | d value (Å) | Strength (%) |
|---|---|---|
| 4.819580 | 18.33540 | 11.85 |
| 9.734293 | 9.08635 | 100.00 |
| 14.642940 | 6.04959 | 2.19 |
| 19.602850 | 4.52869 | 6.36 |
| 21.998290 | 4.04067 | 0.70 |
| 24.522330 | 3.63019 | 0.51 |

Hereinafter, the beneficial effects of the present compound will be further discussed through the stability assays of the amorphous form and the crystal forms. However, it should not be understood that the present compound only has the following beneficial effects.

Assay 1: Stability for Amorphous Form and Crystal Forms of the Present Compound

Tested sample: amorphous form, crystal form I, crystal form II, and crystal form VII of the compound represented by formula (1) were prepared according to Examples;

Test Conditions for Investigating the Influencing Factors:

High temperature tests: amorphous form, crystal form I, crystal form II, and crystal form VII of the compound represented by formula (1) were laid on a dry and clean watch glass, and kept at 60° C.±5° C. for 14 days. Samples were taken respectively on Day 7 and Day 14. The content and the purity of the compound represented by formula (1) were measured, and compared with those of the sample taken on Day 0.

High humidity test: amorphous form, crystal form I, crystal form II, and crystal form VII of the compound represented by formula (1) were laid on a dry and clean watch glass, and kept at 25° C.±2° C., RH75%±5%, 40° C.±2° C., RH75%±5% for 14 days. Samples were taken respectively on Day 7 and Day 14. The content and the purity of the compound represented by formula (1) were measured, and compared with those of the sample taken on Day 0.

Illumination test: amorphous form, crystal form I, crystal form II, and crystal form VII of the compound represented by formula (1) were laid on a dry and clean watch glass, and kept at an illuminance of 4500 Lx±500 Lx in an illumination box for 14 days. Samples were taken respectively on Day 7 and Day 14. The content and the purity of the compound represented by formula (1) were measured, and compared with those of the sample taken on Day 0.

Content: it was measured by using an external standard method in accordance with the High Performance Liquid Chromatography in Chinese Pharmacopoeia, Appendix V D, Edition 2010.

Purity: it was measured by using an area normalization method in accordance with the High Performance Liquid Chromatography in Chinese Pharmacopoeia, Appendix V D, Edition 2010.

Assay 2: Stability for Crystal Form II and Crystal Form IV of the Present Compound Tested sample: crystal form II and crystal form IV of the compound represented by formula (1) were prepared according to Examples;

Test Conditions for Investigating the Influencing Factors:

High temperature tests: crystal form II and crystal form IV of the compound represented by formula (1) were laid on a dry and clean watch glass, and kept at 60° C.±5° C. for 15 days. Samples were taken respectively on Day 5 and Day 15. The content and the purity of the compound represented by formula (1) were measured, and compared with those of the sample taken on Day 0.

High humidity test: crystal form II and crystal form IV of the compound represented by formula (1) were laid on a dry and clean watch glass, and kept at 25° C.±2° C., RH92.5%±5%, 25° C.±2° C., RH75%±5%, 40° C.±2° C., RH75%±5% for 15 days. Samples were taken respectively on Day 5 and Day 15. The content and the purity of the compound represented by formula (1) were measured, and compared with those of the sample taken on Day 0.

Illumination test: crystal form II and crystal form IV of the compound represented by formula (1) were laid on a dry and clean watch glass, and kept at an illuminance of 4500 Lx±500 Lx in an illumination box for 15 days. Samples were taken respectively on Day 5 and Day 15. The content and the purity of the compound represented by formula (1) were measured, and compared with those of the sample taken on Day 0.

Content: it was measured by using an external standard method in accordance with the High Performance Liquid Chromatography in Chinese Pharmacopoeia, Appendix V D, Edition 2010.

TABLE 1

The investigation results of the influencing factor tests for amorphous form and crystal forms of the compound represented by formula (1)

| Test conditions | Test Day | Amorphous form Purity (%) | Amorphous form Content (%) | Crystal form I Purity (%) | Crystal form I Content (%) | Crystal form II Purity (%) | Crystal form II Content (%) | Crystal form VII Purity (%) | Crystal form VII Content (%) |
|---|---|---|---|---|---|---|---|---|---|
| / | Day 0 | 98.0 | 97.1 | 98.2 | 97.0 | 96.4 | 94.5 | 97.4 | 95.8 |
| High temperature 60° C. | Day 7 | 95.8 | 94.5 | 97.9 | 97.7 | 96.1 | 95.8 | 96.8 | 95.2 |
|  | Day 14 | 94.3 | 90.5 | 97.7 | 97.3 | 96.0 | 96.0 | 96.2 | 93.6 |
| 25° C./75% ± 5% RH | Day 7 | 97.1 | 98.7 | 98.1 | 97.2 | 96.3 | 95.9 | 97.1 | 96.1 |
|  | Day 14 | 96.7 | 93.3 | 98.1 | 98.2 | 96.2 | 96.1 | 97.2 | 95.8 |
| 40° C./75% ± 5% RH | Day 7 | 94.9 | 94.7 | 98.0 | 97.4 | 96.2 | 96.5 | 96.4 | 94.6 |
|  | Day 14 | 92.9 | 89.6 | 97.8 | 97.5 | 96.1 | 96.1 | 95.7 | 94.5 |
| Illumination 4500lx ± 500lx | Day 14 | 92.9 | 85.0 | 98.1 | 97.8 | 96.2 | 96.1 | 96.6 | 95.7 |

It could be clear from the investigation results that the content and the purity of amorphous form of the compound represented by formula (1) changed very much at the conditions of high temperature, high humidity and illumination, showing the amorphous form of the compound represented by formula (1) was unstable. However, the content and the purity of crystal forms I, II, VII of the compound represented by formula (1) changed very little at the conditions of high temperature, high humidity and illumination, showing crystal forms I, II, VII of the compound represented by formula (1) had a relatively high stability that was suitable for drug manufacture, storage and transport and was favorable for ensuring the validity and the safety in the drug use.

Purity: it was measured by using an area normalization method in accordance with the High Performance Liquid Chromatography in Chinese Pharmacopoeia, Appendix V D, Edition 2010.

Test results were shown in Table 2.

TABLE 2

The investigation results of the influencing factor tests for crystal forms of the compound represented by formula (1)

| Test conditions | Day | Crystal form II Content % | Crystal form IV Content % |
|---|---|---|---|
| / | 0 | 98.4 | 97.0 |
| 60° C. | 15 | 97.0 | 88.6 |

TABLE 2-continued

The investigation results of the influencing factor tests for crystal forms of the compound represented by formula (1)

| Test conditions | Day | Crystal form II Content % | Crystal form IV Content % |
|---|---|---|---|
| 4500 Lx ± 500 Lx | 15 | 97.8 | 74.6 |
| 25° C./RH 75% ± 5% | 15 | 98.3 | 93.1 |
| 25° C./RH 92.5% ± 5% | 15 | 96.7 | 90.3 |
| 40° C./RH 75% ± 5% | 15 | 98.0 | 74.6 |

It could be clear from the investigation results that the content of the compound represented by formula (1) changed very much, when crystal form IV of the compound represented by formula (1) was in the conditions of high temperature, high humidity and illumination, while the content of the compound represented by formula (1) changed very little, when crystal form II of the compound represented by formula (1) was in the conditions of high temperature, high humidity and illumination, showing crystal form II of the compound represented by formula (1) had higher stability than crystal form IV, and it was suitable for drug manufacture, storage and transport and favorable for ensuring the validity and the safety in the drug use.

The invention claimed is:

1. Crystal forms of a compound represented by formula (1), (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide, Formula (1)

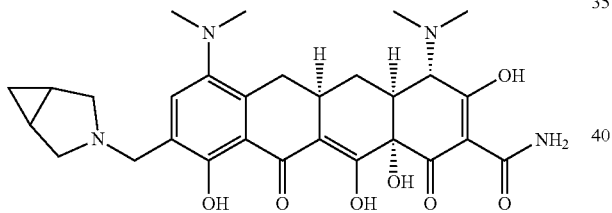

which are characterized by having X-ray powder diffraction patterns comprising the following characteristic peaks expressed by 2θ degree, when measured using Cu-Kα radiation:
Crystal form I: 10.6°±0.2°, 13.3°±0.2°, 15.9°±0.2°, 24.0°±0.2°;
Crystal form II: 10.2°±0.2°, 15.9°±0.2°, 17.9°±0.2°, 24.1°±0.2°;
Crystal form VII: 11.7°±0.2°, 15.1°±0.2°, 15.9°±0.2°, 17.9°±0.2°.

2. Crystal forms of the compound represented by formula (1) of claim 1, which are characterized by having X-ray powder diffraction patterns comprising the following characteristic peaks expressed by 2θ degree, when measured using Cu-Kα radiation:
Crystal form I: 9.0°±0.2°, 10.6°±0.2°, 13.3°±0.2°, 15.9°±0.2°, 23.6°±0.2°, 24.0°±0.2°;
Crystal form II: 9.3°±0.2°, 10.2°±0.2°, 14.0°±0.2°, 15.9°±0.2°, 17.9°±0.2°, 24.1°±0.2°;
Crystal form VII: 11.7°±0.2°, 15.1°±0.2°, 15.9°±0.2°, 17.9°±0.2°, 20.1°±0.2°, 21.8°±0.2°.

3. Crystal forms of the compound represented by formula (1) of claim 1, which are characterized by having X-ray powder diffraction patterns comprising the following characteristic peaks expressed by 2θ degree, when measured using Cu-Kα radiation:
Crystal form I: 9.0°±0.2°, 10.6°±0.2°, 13.3°±0.2°, 14.3°±0.2°, 15.9°±0.2°, 18.0°±0.2°, 20.0°±0.2°, 21.3°±0.2°, 23.6°±0.2°, 24.0°±0.2°;
Crystal form II: 9.3°±0.2°, 10.2°±0.2°, 14.0°±0.2°, 15.9°±0.2°, 17.9°±0.2°, 20.8°±0.2°, 23.0°±0.2°, 24.1°±0.2°, 24.8°±0.2°, 27.7°±0.2°;
Crystal form VII: 11.0°±0.2°, 11.7°±0.2°, 13.8°±0.2°, 14.3°±0.2°, 15.1°±0.2°, 15.9°±0.2°, 17.9°±0.2°, 20.1°±0.2°, 21.8°±0.2°, 25.6°±0.2°.

4. Crystal forms of the compound represented by formula (1) of claim 1, which are characterized in that:
Crystal form I has an X-ray powder diffraction pattern substantially as shown in FIG. 1;
Crystal form II has an X-ray powder diffraction pattern substantially as shown in FIG. 3;
Crystal form VII has an X-ray powder diffraction pattern substantially as shown in FIG. 10.

5. Crystal forms of the compound represented by formula (1) of claim 1, which are characterized in that:
Crystal form I has an endothermic peak in the range of 180-220° C. in its differential scanning calorimetry curve;
Crystal form II has an endothermic peak in the range of 195-215° C. in its differential scanning calorimetry curve;
Crystal form VII has an endothermic peak in the range of 165-205° C. in its differential scanning calorimetry curve.

6. A process for preparing crystal forms I, II, and VII of the compound represented by formula (1) according to claim 1, wherein:
the compound represented by formula (1) is placed in anhydrous acetonitrile for slurry-washing or in tetrahydrofuran for stirring, a solid separates from the mixture, and crystal form I is obtained through filtration;
the compound represented by formula (1) is placed in a lower alcohol, ethyl acetate, acetone, or a mixed solution of methanol and water in a ratio of 1:1-9:1 (v/v) for slurry-washing, or dissolved in tetrahydrofuran under an atmosphere of isopropanol or n-heptane, a solid separates from the mixture, and crystal form II is obtained through filtration;
the compound represented by formula (1) is placed in a mixed solution of acetonitrile and water in a ratio of 1:1-9:1 (v/v) for slurry-washing, filtered, and dried in vacuum to produce crystal form VII.

7. A pharmaceutical composition, wherein said pharmaceutical composition contains crystal form I, II, VII of the compound represented by formula (1) or a combination thereof according to claim 1, and pharmaceutically acceptable carrier(s).

8. The pharmaceutical composition of claim 7, wherein said crystal form has a content of not lower than 94.5%.

9. A pharmaceutical formulation containing crystal form I, II, VII of the compound represented by formula (1) or a combination thereof according to claim 1, and one or more pharmaceutically acceptable carriers and/or diluents, which is in any pharmaceutically acceptable dosage form.

10. A method for treating a disease caused by tetracycline-sensitive bacteria and/or tetracycline-resistant bacteria, comprising:
administering to a recipient in need thereof, an amount of a medicament comprising the crystal form of the compound represented by formula (1) of claim 1, a pharmaceutically acceptable salt, solvate thereof,
wherein said disease caused by tetracycline-sensitive bacteria and/or tetracycline-resistant bacteria is selected from infection, cancer, diabetes and other diseases that have been found to be treatable by other tetracycline compounds, wherein said crystal form is selected from crystal form I, II, VII or a combination thereof.

\* \* \* \* \*